(12) United States Patent
Schulte et al.

(10) Patent No.: US 9,458,223 B2
(45) Date of Patent: Oct. 4, 2016

(54) VON WILLEBRAND FACTOR VARIANTS HAVING IMPROVED FACTOR VIII BINDING AFFINITY

(71) Applicant: CSL BEHRING GMBH, Marburg (DE)

(72) Inventors: Stefan Schulte, Marburg (DE); Thomas Weimer, Gladenbach (DE); Kay Hofmann, Cologne (DE)

(73) Assignee: CSL BEHRING GMBH, Marburg (DE)

( * ) Notice: Subject to any disclaimer, the term of this patent is extended or adjusted under 35 U.S.C. 154(b) by 0 days.

(21) Appl. No.: 14/378,446

(22) PCT Filed: Feb. 14, 2013

(86) PCT No.: PCT/EP2013/052948
§ 371 (c)(1),
(2) Date: Aug. 13, 2014

(87) PCT Pub. No.: WO2013/120939
PCT Pub. Date: Aug. 22, 2013

(65) Prior Publication Data
US 2014/0357564 A1    Dec. 4, 2014

(30) Foreign Application Priority Data
Feb. 15, 2012 (EP) .................... 12155509

(51) Int. Cl.
  *C07K 14/755* (2006.01)
  *A61K 38/00* (2006.01)

(52) U.S. Cl.
  CPC ............. *C07K 14/755* (2013.01); *A61K 38/00* (2013.01)

(58) Field of Classification Search
  CPC .................. A61K 38/00; C07K 14/755
  See application file for complete search history.

(56) References Cited

U.S. PATENT DOCUMENTS

| | | | |
|---|---|---|---|
| 4,970,300 A | 11/1990 | Fulton et al. | |
| 5,408,039 A | 4/1995 | Burnouf-Radosevich et al. | |
| 5,877,152 A | 3/1999 | Fischer et al. | |
| 6,403,077 B1 | 6/2002 | Strom et al. | |
| 2004/0087778 A1 | 5/2004 | Feige et al. | |
| 2010/0183556 A1* | 7/2010 | Choi .................... | C07K 14/755 424/93.2 |

FOREIGN PATENT DOCUMENTS

| | | | | |
|---|---|---|---|---|
| EP | 0 503 991 B1 | 9/1996 | | |
| EP | 0 784 632 B1 | 1/1999 | | |
| JP | 2006101790 A | * | 4/2006 | |
| WO | WO 94/15625 A1 | 7/1994 | | |
| WO | WO 97/03193 A1 | 1/1997 | | |
| WO | WO 97/11957 A1 | 4/1997 | | |
| WO | WO 97/40145 A1 | 10/1997 | | |
| WO | WO 99/55306 A1 | 11/1999 | | |
| WO | WO 0179271 A1 | * | 10/2001 | ........... A61K 9/0019 |
| WO | WO 02/060951 A2 | 8/2002 | | |
| WO | WO 02/103024 A2 | 12/2002 | | |
| WO | WO 03/076567 A2 | 9/2003 | | |
| WO | WO 03/087355 A1 | 10/2003 | | |
| WO | WO 03/093313 A2 | 11/2003 | | |
| WO | WO 2004/075923 A2 | 9/2004 | | |
| WO | WO 2004/101740 A2 | 11/2004 | | |
| WO | WO 2005/000892 A2 | 1/2005 | | |
| WO | WO 2005/001025 A2 | 1/2005 | | |
| WO | WO 2005/063808 A1 | 7/2005 | | |
| WO | WO 2006/000448 A2 | 1/2006 | | |
| WO | WO 2006/071801 A2 | 7/2006 | | |
| WO | WO 2006/108590 A1 | 10/2006 | | |
| WO | WO 2007/090584 A1 | 8/2007 | | |
| WO | WO 2007/126808 A1 | 11/2007 | | |
| WO | WO 2007/144173 A1 | 12/2007 | | |
| WO | WO 2008/005290 A2 | 1/2008 | | |
| WO | WO 2008/077616 A1 | 7/2008 | | |
| WO | WO 2009/156137 A1 | 12/2009 | | |
| WO | WO 2011020866 A2 | * | 2/2011 | ........... A61K 9/0019 |

OTHER PUBLICATIONS

UniProt Protein Database, protein Q28834, Von Willebrand Factor, accessed Jun. 14, 2015.*
Uniprot Protein Database, Protein Accession L8E853, von Willeband Factor, human, accessed on Oct. 28, 2015.*
L. Hilbert, Expression of two type 2N von Willebrand disease mutations identified in exon 18 of von Willebrand factor gene Von Willebrand factor (VWF) is a large, multimeric glycoprotein with two main roles in haemostasis. It mediates platelet adhesion,, British Journal of Haematology, 127, 184-189, 2004.*
Uniprot Protein Database, Protein Accession P04275, von Willeband Factor, human, accessed on Oct. 29, 2015.*
JP2006-101790 A, English Translation accessed on May 2, 2016, Japanese Platform for Patent Information website.*
JP2006-101790A, Sequence listing, pp. 1-190, accessed on Japanese Platform for Patent Information website, May 2, 2016.*
Voorberg, J. et al., "Domains Involved in Multimer Assembly of von Willebrand factor (vWF): multimerization is independent of dimerization", The EMBO Journal, vol. 9, No. 3, pp. 797-803 (1990).
Dang, L.T., et al., "Phylogenetic and Functional Analysis of Histidine Residues Essential for pH-dependent Multimerization of von Willebrand Factor", The Journal of Biological Chemistry, vol. 286, No. 29, pp. 25763-25769 (2011).
Rizza, C.R., et al., "Coagulation Assay of VIIIC and IXC", in: Bloom AL, ed., The Hemophilias, Edinburgh: Churchill Livingstone, pp. 18-38 (1982).
Rosen, S., "Assay of Factor VIII: C with a Chromogenic Substrate", Scand J Haematol, Suppl. 40, vol. 33, pp. 139-145 (1984).
Collins, C.J., et al., "Molecular Closing of the Human Gene for von Willebrand Factor and Identification of the Transcription Initiation Site", Proc. Natl., Acad. Sci, USA, vol. 84, pp. 4393-4397 (1987).

(Continued)

*Primary Examiner* — James H Alstrum Acevedo
*Assistant Examiner* — Erinne Dabkowski
(74) *Attorney, Agent, or Firm* — Finnegan, Henderson, Farabow, Garrett & Dunner, LLP

(57) ABSTRACT

The present invention relates to a polypeptide comprising a modified von Willebrand Factor (VWF) having a higher Factor VIII binding affinity than non-modified VWF, its pharmaceutical use and method of its preparation.

20 Claims, No Drawings

(56) References Cited

OTHER PUBLICATIONS

Kaufman, R. J., et al., "Effect of von Willebrand Factor Coexpression on the Synthesis and Secretion of Factor VIII in Chinese Hamster Ovary Cells", Molecular and Cellular Biology, vol. 9, No. 3, p. 1233-1242 (1989).
Leyte, A., et al., "The Interaction Between Human Blood-Coagulation Factor VIII and Von Willebrand Factor", Biochem, J., vol. 257, pp. 679-683 (1989).
Fischer, B., et al., "Structural Analysis of Recombinant von Willebrand Factor: Identification of Hetero- and Homo-dimers", FEBS Letters, vol. 351, pp. 345-348 (1994).
Vlot, A.J., et al., "The Affinity and Stoichiometry of Binding of Human Factor VII to von Willebrand Factor", Blood, vol. 85, No. 11, pp. 3150-3157 (1995).
Swaroop, M., et al., "Mutagenesis of a Potential Immunoglobulin-binding Protein-binding Site Enhances Secretion of Coagulation Factor VIII", The Journal of Biological Chemistry, vol. 272, No. 39, pp. 24121-24124 (1997).
Amano, K., et al., "Mutation at Either Arg336 or Arg562 in Factor VIII is Insufficient for Complete Resistance to Activated Protein C (APC)-mediated Inactivation: Implications for the APC Resistance Test", Thromb. Haemost., vol. 79, No. 3, pp. 557-563 (1998).
Lollar, P., "Characterization of Factor VIII B-Cell Inhibitory Epitopes", Thromb. Haemost., vol. 82, No. 2, pp. 505-508 (1999).
Oh, S.-H. et al., "Synthesis of Recombinant Blood Coagulation Factor VIII (FVIII) Heavy and Light Chains and Reconstitution of Active Form of FVIII," Experimental & Molecular Medicine, vol. 31, pp. 95-100 (1999).
Ananyeva, N.M., et al., "Catabolism of the Coagulation Factor VIII", TCM vol. 11, No. 6, pp. 251-257 (2001).
Kallas, A., et al., "The von Willebrand Factor Collagen-Binding Activity Assay: Clinical Application", Ann Hematol, vol. 80, pp. 466-471 (2001).
Federici, A., et al., "A Sensitive Ristocetin Co-Factor Activity Assay With Recombinant Glycoprotein Ibα for the Diagnosis of Patients with Low von Willebrand Factor Levels", Haematologica 89(1), pp. 77-86 (2004).
Miao, H.Z. et al., "Bioengineering of Coagulation Factor VIII for Improved Secretion", Blood, vol. 103, No. 9, pp. 3412-3419 (2004).
Pipe, S.W., "Coagulation Factors with Improved Properties for Hemophilia Gene Therapy", Seminars in Thrombosis and Hemosasis, vol. 30, No. 2, pp. 227-237 (2004).
Wakabayashi, H., et al., "A Glu 113Ala Mutation within a Factor VIII $Ca^{2+}$-Binding Site Enhances Cofactor Interactions in Factor Xase", Biochemistry, vol. 44, No. 30, pp. 10298-10304 (2005).
Dumont, J.A., et al., "Monomeric Fc Fusions", Biodrugs, vol. 20, No. 3, pp. 151-160 (2006).
Gale, A.J., et al., "Intrinsic Stability and Functional Properties of Disulfide Bond-Stabilized Coagulation Factor VIIIa Variants", Journal of Thrombosis and Haemostasis, vol. 4, pp. 1315-1322 (2006).
Sucker, C., et al., "Determination of von Willebrand Factor Activity: Evaluation of HaemosIL™ Assay in Comparison With Established Procedures", Clin Appl Thromb Haemost, vol. 12, pp. 305-310 (2006).
International Preliminary Report on Patentability for International Application No. PCT/EP2013/052948 dated Aug. 28, 2014 (6 pages).
International Search Report for International Application No. PCT/EP2013/052948 dated Mar. 22, 2013 (12 pages).
European Search Report for European Patent Application No. 12155509.8 dated May 22, 2012 (6 pages).
Australian Patent Examination Report No. 3 for Australian Patent Application No. 2013200843, dated Aug. 22, 2014 (3 pages).

\* cited by examiner

VON WILLEBRAND FACTOR VARIANTS HAVING IMPROVED FACTOR VIII BINDING AFFINITY

FIELD OF THE INVENTION

The present invention relates to a polypeptide comprising a modified von Willebrand Factor which exhibits improved binding affinity to Factor VIII. The invention further relates to a complex comprising the polypeptide and FVIII, to a polynucleotide encoding the polypeptide of the invention and a method of producing the polypeptide. Furthermore, the invention concerns the therapeutic or prophylactic use of the polypeptide or complex of the invention for treating bleeding disorders.

BACKGROUND OF THE INVENTION

There are various bleeding disorders caused by deficiencies of blood coagulation factors. The most common disorders are hemophilia A and B, resulting from deficiencies of blood coagulation factor VIII and IX, respectively. Another known bleeding disorder is von Willebrand's disease.

In plasma FVIII exists mostly as a noncovalent complex with VWF and its coagulant function is to accelerate factor IXa dependent conversion of factor X to Xa. Due to the complex formation of FVIII and VWF it was assumed for a long time that FVIII and VWF functions are two functions of the same molecule. Only in the seventies it became clear that FVIII and VWF are separate molecules that form a complex under physiologic conditions. In the eighties then the dissociation constant of about 0.2 nmol/L was determined (Leyte et al., Biochem J 1989, 257: 679-683) and the DNA sequence of both molecules was studied.

Classic hemophilia or hemophilia A is an inherited bleeding disorder. It results from a chromosome X-linked deficiency of blood coagulation FVIII, and affects almost exclusively males with an incidence of between one and two individuals per 10.000. The X-chromosome defect is transmitted by female carriers who are not themselves hemophiliacs. The clinical manifestation of hemophilia A is an increased bleeding tendency. Before treatment with FVIII concentrates was introduced the mean life span for a person with severe hemophilia was less than 20 years. The use of concentrates of FVIII from plasma has considerably improved the situation for the hemophilia A patients increasing the mean life span extensively, giving most of them the possibility to live a more or less normal life. However, there have been certain problems with the plasma derived concentrates and their use, the most serious of which have been the transmission of viruses. So far, viruses causing hepatitis B, non-A non-B hepatitis and AIDS have hit the population seriously. Since then different virus inactivation methods and new highly purified FVIII concentrates have recently been developed which established a very high safety standard also for plasma derived FVIII.

In severe hemophilia A patients undergoing prophylactic treatment FVIII has to be administered intravenously (i.v.) about 3 times per week due to the short plasma half-life of FVIII of about 12 to 14 hours. Each i.v. administration is cumbersome, associated with pain and entails the risk of an infection especially as this is mostly done at home by the patients themselves or by the parents of children being diagnosed for hemophilia A.

It would thus be highly desirable to create a FVIII with increased functional half-life allowing the manufacturing of pharmaceutical compositions containing FVIII, which have to be administered less frequently.

Several attempts have been made to prolong the half-life of non-activated FVIII either by reducing its interaction with cellular receptors (WO 03/093313A2, WO 02/060951A2), by covalently attaching polymers to FVIII (WO 94/15625, WO 97/11957 and U.S. Pat. No. 4,970,300), by encapsulation of FVIII (WO 99/55306), by introduction of novel metal binding sites (WO 97/03193), by covalently attaching the A2 domain to the A3 domain either by peptidic (WO 97/40145 and WO 03/087355) or disulfide linkage (WO 02/103024A2) or by covalently attaching the A1 domain to the A2 domain (WO2006/108590).

Another approach to enhance the functional half-life of FVIII or VWF is by PEGylation of FVIII (WO 2007/126808, WO 2006/053299, WO 2004/075923) or by PEGylation of VWF (WO 2006/071801) which pegylated VWF by having an increased half-life would indirectly also enhance the half-life of FVIII present in plasma. Also fusion proteins of FVIII have been described (WO 2004/101740, WO2008/077616 and WO 2009/156137).

VWF, which is missing, functionally defect or only available in reduced quantity in different forms of von Willebrand disease (VWD), is a multimeric adhesive glycoprotein present in the plasma of mammals, which has multiple physiological functions. During primary hemostasis VWF acts as a mediator between specific receptors on the platelet surface and components of the extracellular matrix such as collagen. Moreover, VWF serves as a carrier and stabilizing protein for procoagulant FVIII. VWF is synthesized in endothelial cells and megakaryocytes as a 2813 amino acid precursor molecule. The amino acid sequence and the cDNA sequence of wild-type VWF are disclosed in Collins et al. 1987, Proc Natl. Acad. Sci. USA 84:4393-4397. The precursor polypeptide, pre-pro-VWF, consists of a 22-residue signal peptide, a 741-residue pro-peptide and the 2050-residue polypeptide found in mature plasma VWF (Fischer et al., FEBS Lett. 351: 345-348, 1994). After cleavage of the signal peptide in the endoplasmatic reticulum a C-terminal disulfide bridge is formed between two monomers of VWF. During further transport through the secretory pathway 12 N-linked and 10 O-linked carbohydrate side chains are added. More important, VWF dimers are multimerized via N-terminal disulfide bridges and the propeptide of 741 amino acids length is cleaved off by the enzyme PACE/furin in the late Golgi apparatus. The propeptide as well as the high-molecular-weight multimers of VWF (VWF-HMWM) are stored in the Weibel-Pallade bodies of endothelial cells or in the α-Granules of platelets.

Once secreted into plasma the protease ADAMTS13 cleaves VWF within the A1 domain of VWF. Plasma VWF therefore consists of a whole range of multimers ranging from single dimers of 500 kDa to multimers consisting of up to more than 20 dimers of a molecular weight of over 10,000 kDa. The VWF-HMWM hereby having the strongest hemostatic activity, which can be measured in ristocetin cofactor activity (VWF:RCo). The higher the ratio of VWF:RCo/VWF antigen, the higher the relative amount of high molecular weight multimers.

Defects in VWF are causal to von Willebrand disease (VWD), which is characterized by a more or less pronounced bleeding phenotype. VWD type 3 is the most severe form in which VWF is completely missing, VWD type 1 relates to a quantitative loss of VWF and its phenotype can be very mild. VWD type 2 relates to qualitative defects of VWF and can be as severe as VWD type 3. VWD type 2 has many sub forms some of them being associated with the loss or the decrease of high molecular weight multimers. Von VWD type 2a is characterized by a loss of both intermediate and large multimers. VWD type 2B is characterized by a loss of highest-molecular-weight multimers.

VWD is the most frequent inherited bleeding disorder in humans and can be treated by replacement therapy with concentrates containing VWF of plasmatic or recombinant origin. VWF can be prepared from human plasma as for example described in EP 05503991. EP 0784632 describes a method for isolating recombinant VWF.

In plasma FVIII binds with high affinity to von VWF, which protects it from premature catabolism and thus, plays in addition to its role in primary hemostasis a crucial role to regulate plasma levels of FVIII and as a consequence is also a central factor to control secondary hemostasis. The half-life of non-activated FVIII bound to VWF is about 12 to 14 hours in plasma. In von Willebrand disease type 3, where no or almost no VWF is present, the half-life of FVIII is only about 6 hours, leading to symptoms of mild to moderate hemophilia A in such patients due to decreased concentrations of FVIII. The stabilizing effect of VWF on FVIII has also been used to aid recombinant expression of FVIII in CHO cells (Kaufman et al. 1989, Mol Cell Biol).

There is a need for VWF molecules having improved affinity to FVIII in order to stabilize FVIII. It was surprisingly found that mutations in the D' domain of VWF can increase the affinity of VWF to FVIII. This allows providing FVIII/VWF complexes having a high affinity which are advantageous in therapy and prophylaxis of bleeding disorder.

SUMMARY OF THE INVENTION

In a first aspect the present invention relates to a polypeptide comprising a modified von Willebrand Factor (VWF),
wherein the amino acid sequence of said modified VWF has at least one mutation within the D' domain relative to the amino acid sequence of the D' domain of wild type VWF as shown in SEQ ID NO:31,
and wherein the binding affinity of said polypeptide comprising a modified VWF to Factor VIII (FVIII) is higher than that of a reference polypeptide, wherein the amino acid sequence of said reference polypeptide is identical to the amino acid sequence of said polypeptide comprising a modified VWF except that the amino acid sequence of the D' domain of the reference polypeptide consists of SEQ ID NO:31.

According to a preferred embodiment of the first aspect, the Factor VIII binding affinity of the polypeptide exceeds that of the reference polypeptide by at least 10 percent.

In another preferred embodiment, the affinity constant $K_A$ for binding of the polypeptide to wild type Factor VIII is at least $3 \times 10^{10}$ $M^{-1}$.

In one aspect, the invention relates to a polypeptide comprising a modified von Willebrand Factor (VWF),
wherein the amino acid sequence of said modified VWF has at least one substitution within the D' domain relative to the amino acid sequence of the D' domain of wild type VWF as shown in SEQ ID NO:31,
wherein said substitution replaces a negatively charged amino acid present in the D' domain of wild type VWF as shown in SEQ ID NO:31 with a neutral amino acid or with a positively charged amino acid.

In another aspect, the invention relates to a polypeptide comprising a modified von Willebrand Factor (VWF),
wherein the amino acid sequence of said modified VWF has at least one substitution within the D' domain relative to the amino acid sequence of the D' domain of wild type VWF as shown in SEQ ID NO:31,
wherein said substitution replaces a neutral amino acid present in the D' domain of wild type VWF as shown in SEQ ID NO:31 with a positively charged amino acid.

It is preferred that the mutation within the D' domain includes an amino acid substitution at one of positions 779, 781, 787, 789, 793, 794, 796, 798, 802, 818, 819, 825, 835, 838 and 853 of the VWF amino acid sequence as shown in SEQ ID NO:2.

It is further preferred that the mutation within the D' domain includes an amino acid substitution at one of positions 779, 781, 789, 793, 794, 802, 818, 819, 835, 838 and 853 of the VWF amino acid sequence as shown in SEQ ID NO:2. For example, the amino acid substitution within the D' domain may be selected from the group consisting of Asp779Asn, Leu781 Pro, Glu787Gln, Thr789Ala, Gln793Arg, Asn794Lys, Asp796Ala, Glu798Gln, Met802Arg, Met802Lys, Glu818Ala, Glu818Lys, Asn819Lys, Glu825Lys, Glu835Gln, Pro838Lys, and Asp853Asn, wherein the numbering refers to SEQ ID NO:2.

In another embodiment, the polypeptide comprises an amino acid sequence as shown in SEQ ID NO:33 or SEQ ID NO:34, with the proviso that the D' domain of the modified VWF contains at least one substitution relative to SEQ ID NO:31. For example, the polypeptide may comprise an amino acid sequence as shown in SEQ ID NO:35, with the proviso that the D' domain of the modified VWF contains at least one substitution relative to SEQ ID NO:31.

In another embodiment, the polypeptide of the present invention comprises an amino acid sequence as shown in SEQ ID NO:2 with the proviso that the D' domain of the modified VWF contains at least one amino acid substitution which increased FVIII binding by improving electrostatic attraction between the VWF polypeptide of the invention and FVIII, characterized in that acidic residues of the VWF D' domain are replaced by neutral or basic amino acids or neutral residues are replaced by basic amino acids.

In another preferred embodiment, the polypeptide of the present invention further comprises a half-life enhancing protein (HLEP). Preferrably, the HLEP is an albumin. The N-terminus of the albumin may be fused to the C-terminus of the VWF amino acid sequence.

A second aspect of the present invention is a complex comprising a Factor VIII molecule and a polypeptide of the present invention. Preferably, the complex has a dissociation constant $K_D$ of 0.2 nmol/L or less. More preferably, the Factor VIII in the complex is the polypeptide of SEQ ID NO:37.

Yet another aspect of the present invention is the polypeptide of the present invention or the complex of the present invention for use in the treatment or prophylaxis of a bleeding disorder, e.g. of von Willebrand's disease (VWD) or hemophilia.

Yet another aspect of the present invention is a pharmaceutical composition comprising the polypeptide of the present invention or the complex of the present invention.

In another aspect, the invention relates to a method of treating a bleeding disorder, comprising administering to a patient in need thereof, a pharmaceutically effective amount of the polypeptide of the present invention or of the complex of the present invention. Preferably, the bleeding disorder is VWD or hemophilia A.

In yet another aspect the invention relates to a polynucleotide encoding the polypeptide of the present invention.

In another aspect, the invention pertains to a plasmid or vector comprising the polynucleotide of the present invention. The plasmid or vector is preferably an expression plasmid or expression vector.

In another aspect, the invention concerns a host cell comprising the polynucleotide or the plasmid of the present invention.

The invention further includes a method of producing a polypeptide comprising a modified VWF, comprising
(a) culturing the host cells of the present invention under conditions such that the polypeptide comprising a modified VWF is expressed; and
(b) optionally recovering the polypeptide comprising a modified VWF from the host cells or from the culture medium.

Yet another aspect of this invention is a method of increasing the Factor VIII binding affinity of VWF, comprising introducing a mutation into the D' domain of the VWF amino acid sequence, which is not present in the amino acid sequence of the D' domain of wild type VWF as shown in SEQ ID NO:31.

In another aspect, the invention relates to the use of a modified VWF having a higher affinity to FVIII than non-modified VWF for increasing the half-life of FVIII. The modified VWF is preferably a polypeptide of the invention as defined herein, or a modified VWF as defined herein. More preferably, the modified VWF is a fusion protein, most preferably an albumin fusion protein.

A further aspect of the invention is a method of preparing a complex comprising Factor VIII and VWF, said method comprising mixing a Factor VIII molecule with the polypeptide of the present invention or its half-life extended version.

DETAILED DESCRIPTION

The polypeptide of the present invention comprises a modified von Willebrand Factor.

VWF

The term "von Willebrand Factor" or "VWF", as used herein, refers to any polypeptide having the biological activity of wild type VWF. The gene encoding wild type VWF is transcribed into a 9 kb mRNA which is translated into a pre-propolypeptide of 2813 amino acids with an estimated molecular weight of 310,000 Da. The pre-propolypeptide contains a 22 amino acids signal peptide, a 741 amino acid pro-polypeptide and the mature subunit. Cleavage of the 741 amino acids propolypeptide from the N-terminus results in mature VWF consisting of 2050 amino acids. The amino acid sequence of the VWF pre-propolypeptide is shown in SEQ ID NO:2. Unless indicated otherwise, the amino acid numbering of VWF residues in this application refers to SEQ ID NO:2, even if the VWF molecule does not need to comprise all residues of SEQ ID NO:2. The amino acid sequence of mature VWF is shown in SEQ ID NO:32. The term "VWF" as used herein refers to the mature form of VWF unless indicated otherwise.

The propolypeptide of wild type VWF comprises multiple domains which are arranged in the following order:

D1-D2-D'-D3-A1-A2-A3-D4-B1-B2-B3-C1-C2-CK

The D1 and D2 domain represent the propeptide which is cleaved off to yield the mature VWF. The D' domain encompasses amino acids 764 to 865 of SEQ ID NO:2. The amino acid sequence of the D' domain of wild type VWF is shown in SEQ ID NO:31. The carboxylterminal 90 residues comprise the "CK" domain that is homologous to the "cystine knot" superfamily of protein. These family members have a tendency to dimerise through disulfide bonds.

Preferably, wild type VWF comprises the amino acid sequence of mature VWF as shown in SEQ ID NO:32. Also encompassed are additions, insertions, N-terminal, C-terminal or internal deletions of VWF as long as the biological activity of VWF is retained. The biological activity is retained in the sense of the invention if the VWF with deletions retains at least 10%, preferably at least 25%, more preferably at least 50%, most preferably at least 75% of the biological activity of wild-type VWF. The biological activity of wild-type VWF can be determined by the artisan using methods for ristocetin co-factor activity (Federici A B et al. 2004. Haematologica 89:77-85), binding of VWF to GP Ibα of the platelet glycoprotein complex Ib-V-IX (Sucker et al. 2006. Clin Appl Thromb Hemost. 12:305-310), or a collagen binding assay (Kallas & Talpsep. 2001. Annals of Hematology 80:466-471).

Factor VIII

The terms "blood coagulation Factor VIII", "Factor VIII" and "FVIII" are used interchangeably herein. "Blood coagulation Factor VIII" includes wild-type blood coagulation FVIII as well as derivatives of wild-type blood coagulation FVIII having the procoagulant activity of wild-type blood coagulation FVIII. Derivatives may have deletions, insertions and/or additions compared with the amino acid sequence of wild-type FVIII. The term FVIII includes proteolytically processed forms of FVIII, e.g. the form before activation, comprising heavy chain and light chain.

The term "FVIII" includes any FVIII variants or mutants having at least 25%, more preferably at least 50%, most preferably at least 75% of the biological activity of wild-type factor VIII.

As non-limiting examples, FVIII molecules include FVIII mutants preventing or reducing APC cleavage (Amano 1998. Thromb. Haemost. 79:557-563), FVIII mutants further stabilizing the A2 domain (WO 97/40145), FVIII mutants resulting in increased expression (Swaroop et al. 1997. JBC 272:24121-24124), FVIII mutants reducing its immunogenicity (Lollar 1999. Thromb. Haemost. 82:505-508), FVIII reconstituted from differently expressed heavy and light chains (Oh et al. 1999. Exp. Mol. Med. 31:95-100), FVIII mutants reducing binding to receptors leading to catabolism of FVIII like HSPG (heparan sulfate proteoglycans) and/or LRP (low density lipoprotein receptor related protein) (Ananyeva et al. 2001. TCM, 11:251-257), disulfide bond-stabilized FVIII variants (Gale et al., 2006. J. Thromb. Hemost. 4:1315-1322), FVIII mutants with improved secretion properties (Miao et al., 2004. Blood 103:3412-3419), FVIII mutants with increased cofactor specific activity (Wakabayashi et al., 2005. Biochemistry 44:10298-304), FVIII mutants with improved biosynthesis and secretion, reduced ER chaperone interaction, improved ER-Golgi transport, increased activation or resistance to inactivation and improved half-life (summarized by Pipe 2004. Sem. Thromb. Hemost. 30:227-237). All of these FVIII mutants and variants are incorporated herein by reference in their entirety.

Preferably FVIII comprises the full length sequence of FVIII as shown in SEQ ID NO:36. Also encompassed are additions, insertions, substitutions, N-terminal, C-terminal or internal deletions of FVIII as long as the biological activity of FVIII is retained. The biological activity is retained in the sense of the invention if the FVIII with modifications retains at least 10%, preferably at least 25%, more preferably at least 50%, most preferably at least 75% of the biological activity of wild-type FVIII. The biological activity of FVIII can be determined by the artisan as described below.

A suitable test to determine the biological activity of FVIII is for example the one stage or the two stage coagulation assay (Rizza et al. 1982. Coagulation assay of FVIII:C and FIXa in Bloom ed. The Hemophilias. NY Churchchill Livingston 1992) or the chromogenic substrate FVIII:C assay (S. Rosen, 1984. Scand J Haematol 33: 139-145, suppl.). The content of these references is incorporated herein by reference.

The amino acid sequence of the mature wild-type form of human blood coagulation FVIII is shown in SEQ ID NO:36. The reference to an amino acid position of a specific sequence means the position of said amino acid in the FVIII wild-type protein and does not exclude the presence of mutations, e.g. deletions, insertions and/or substitutions at other positions in the sequence referred to. For example, a mutation in "Glu2004" referring to SEQ ID NO:36 does not exclude that in the modified homologue one or more amino acids at positions 1 through 2332 of SEQ ID NO:36 are missing.

"FVIII" and/or "VWF" within the above definition also include natural allelic variations that may exist and occur from one individual to another. "FVIII" and/or "VWF" within the above definition further includes variants of FVIII and or VWF. Such variants differ in one or more amino acid residues from the wild-type sequence. Examples of such differences may include as conservative amino acid substitutions, i.e. substitutions within groups of amino acids with similar characteristics, e.g. (1) small amino acids, (2) acidic amino acids, (3) polar amino acids, (4) basic amino acids, (5) hydrophobic amino acids, and (6) aromatic amino acids. Examples of such conservative substitutions are shown in the following table 1.

TABLE 1

| (1) Alanine | Glycine | | |
|---|---|---|---|
| (2) Aspartic acid | Glutamic acid | | |
| (3) Asparagine | Glutamine | Serine | Threonine |
| (4) Arginine | Histidine | Lysine | |
| (5) Isoleucine | Leucine | Methionine | Valine |
| (6) Phenylalanine | Tyrosine | Tryptophane | |

Modified VWF

The modified VWF of the present invention has an amino acid sequence which differs from that of wild-type VWF. According to the present invention the modified VWF has at least one mutation within its D' domain, as compared to the amino acid sequence of the D' domain of wild-type VWF as shown in SEQ ID NO:31. The mutation may be a deletion, insertion or substitution. Preferably, the mutation is an amino acid substitution.

The amino acid sequence of the D' domain of the modified VWF can have one or more mutations relative to SEQ ID NO:31. The amino acid sequence of the D' domain of the modified VWF may have one, two, three, four, five or more mutations relative to SEQ ID NO:31. It is preferred that the amino acid sequence of the D' domain of the modified VWF has one, two or three mutations relative to SEQ ID NO:31. Most preferably, the amino acid sequence of the D' domain of the modified VWF has exactly one substitution relative to the amino acid sequence as shown in SEQ ID NO:31.

In a first approach, the amino acid positions which are preferably mutated in the modified VWF increase the positive charge of the D' domain and/or reduce the negative charge thereof. This first approach is referred to herein as "electrostatic approach". This can be achieved by replacing at least one amino acid having a negative charge at pH 7.4 with at least one amino acid which is neutral or has a positive charge at pH 7.4. Alternatively, this can be achieved by replacing at least one amino acid which is neutral at pH 7.4 with at least one amino acid having a positive charge at pH 7.4. These amino acid types are defined as follows:

Amino acids having a negative charge at pH 7.4 are aspartic acid (aspartate) and glutamic acid (glutamate); they are referred to as "negatively charged amino acids" hereinafter.

Amino acids having a positive charge at pH 7.4 are lysine and arginine; they are referred to as "positively charged amino acids" hereinafter.

Amino acids which are neutral at pH 7.4 are alanine, glycine, asparagine, glutamine, serine, threonine, histidine, isoleucine, leucine, methionine, valine, phenylalanine, tyrosine, tryptophane, proline, and cysteine; they are referred to as "neutral amino acids" hereinafter.

In one aspect of the electrostatic approach, the invention relates to a polypeptide comprising a modified von Willebrand Factor (VWF), wherein the amino acid sequence of said modified VWF has at least one substitution within the D' domain relative to the amino acid sequence of the D' domain of wild type VWF as shown in SEQ ID NO:31, wherein said substitution replaces a negatively charged amino acid present in the D' domain of wild type VWF as shown in SEQ ID NO:31 with a neutral amino acid or with a positively charged amino acid.

In another aspect of the electrostatic approach, the invention relates to a polypeptide comprising a modified von Willebrand Factor (VWF), wherein the amino acid sequence of said modified VWF has at least one substitution within the D' domain relative to the amino acid sequence of the D' domain of wild type VWF as shown in SEQ ID NO:31, wherein said substitution replaces a neutral amino acid present in the D' domain of wild type VWF as shown in SEQ ID NO:31 with a positively charged amino acid.

The modified VWF of the present invention includes, but is not limited to, the following embodiments in accordance with the electrostatic approach which can be combined with each other.

In a first embodiment in accordance with the electrostatic approach, the amino acid at position 779 of the VWF amino acid sequence is a neutral amino acid or a positively charged amino acid. The amino acid at position 779 of the VWF amino acid sequence may be lysine. Alternatively, the amino acid at position 779 of the VWF amino acid sequence may be arginine. Alternatively, the amino acid at position 779 of the VWF amino acid sequence may be a neutral amino acid.

In a second embodiment in accordance with the electrostatic approach, the amino acid at position 787 of the VWF amino acid sequence is a neutral amino acid or a positively charged amino acid. The amino acid at position 787 of the VWF amino acid sequence may be lysine. Alternatively, the amino acid at position 787 of the VWF amino acid sequence may be arginine. Alternatively, the amino acid at position 787 of the VWF amino acid sequence may be a neutral amino acid.

In a third embodiment in accordance with the electrostatic approach, the amino acid at position 793 of the VWF amino acid sequence is a positively charged amino acid. The amino acid at position 793 of the VWF amino acid sequence may be lysine. Alternatively, the amino acid at position 793 of the VWF amino acid sequence may be arginine.

In a fourth embodiment in accordance with the electrostatic approach, the amino acid at position 794 of the VWF amino acid sequence is a positively charged amino acid. The amino acid at position 794 of the VWF amino acid sequence may be lysine. Alternatively, the amino acid at position 794 of the VWF amino acid sequence may be arginine.

In a fifth embodiment in accordance with the electrostatic approach, the amino acid at position 796 of the VWF amino acid sequence is a neutral amino acid or a positively charged amino acid. The amino acid at position 796 of the VWF amino acid sequence may be lysine. Alternatively, the amino acid at position 796 of the VWF amino acid sequence may be arginine. Alternatively, the amino acid at position 796 of the VWF amino acid sequence may be a neutral amino acid.

In a sixth embodiment in accordance with the electrostatic approach, the amino acid at position 798 of the VWF amino acid sequence is a neutral amino acid or a positively charged amino acid. The amino acid at position 798 of the VWF amino acid sequence may be lysine. Alternatively, the amino acid at position 798 of the VWF amino acid sequence may be arginine. Alternatively, the amino acid at position 798 of the VWF amino acid sequence may be a neutral amino acid.

In a seventh embodiment in accordance with the electrostatic approach, the amino acid at position 802 of the VWF amino acid sequence is a positively charged amino acid. The amino acid at position 802 of the VWF amino acid sequence may be lysine. Alternatively, the amino acid at position 802 of the VWF amino acid sequence may be arginine.

In an eighth embodiment in accordance with the electrostatic approach, the amino acid at position 818 of the VWF amino acid sequence is a neutral amino acid or a positively charged amino acid. The amino acid at position 818 of the VWF amino acid sequence may be lysine. Alternatively, the amino acid at position 818 of the VWF amino acid sequence may be arginine. Alternatively, the amino acid at position 818 of the VWF amino acid sequence may be a neutral amino acid.

In a ninth embodiment in accordance with the electrostatic approach, the amino acid at position 819 of the VWF amino acid sequence is a positively charged amino acid. The amino acid at position 819 of the VWF amino acid sequence may be lysine. Alternatively, the amino acid at position 819 of the VWF amino acid sequence may be arginine.

In a tenth embodiment in accordance with the electrostatic approach, the amino acid at position 825 of the VWF amino acid sequence is a neutral amino acid or a positively charged amino acid. The amino acid at position 825 of the VWF amino acid sequence may be lysine. Alternatively, the amino acid at position 825 of the VWF amino acid sequence may be arginine. Alternatively, the amino acid at position 825 of the VWF amino acid sequence may be a neutral amino acid.

In an eleventh embodiment in accordance with the electrostatic approach, the amino acid at position 835 of the VWF amino acid is a neutral amino acid or a positively charged amino acid. The amino acid at position 835 of the VWF amino acid sequence may be lysine. Alternatively, the amino acid at position 835 of the VWF amino acid sequence may be arginine. Alternatively, the amino acid at position 835 of the VWF amino acid sequence may be a neutral amino acid.

In a twelfth embodiment in accordance with the electrostatic approach, the amino acid at position 838 of the VWF amino acid sequence is a positively charged amino acid. The amino acid at position 838 of the VWF amino acid sequence may be lysine. Alternatively, the amino acid at position 838 of the VWF amino acid sequence may be arginine.

In a thirteenth embodiment, the amino acid at position 853 of the VWF amino acid sequence is a neutral amino acid or a positively charged amino acid. The amino acid at position 853 of the VWF amino acid sequence may be lysine. Alternatively, the amino acid at position 853 of the VWF amino acid sequence may be arginine. Alternatively, the amino acid at position 853 of the VWF amino acid sequence may be a neutral amino acid.

In an alternative second approach, an amino acid in the D' domain may be replaced with a different amino acid which is evolutionarily conserved or at least polymorphic at the respective position. This second approach is referred to as "evolutionary approach" hereinafter.

Replacing with a different amino acid which is evolutionarily conserved in the sense of the invention means that a given amino acid within the D' domain which is present (i) only in humans is replaced with a different amino acid which is conserved in other species at the respective amino acid position, or (ii) which is present only in humans and some other species but not in most species is replaced with the more abundant respective amino acid which is present in most other species, or (iii) is common human polymorphism. This means that at least one residue of the VWF D' domain is replaced with a different amino acid which is present at the same position in one or more VWF polymorphs or orthologues having a D' domain different from SEQ ID NO:31.

The modified VWF of the present invention includes, but is not limited to, the following embodiments in accordance with the evolutionary approach which can be combined with each other and with any embodiment(s) of the electrostatic approach.

In a first embodiment in accordance with the evolutionary approach, the amino acid at position 781 of the VWF amino acid sequence is a proline.

In a second embodiment in accordance with the evolutionary approach, the amino acid at position 789 of the VWF amino acid sequence is alanine, glycine, serine or valine.

In other preferred embodiments of the invention the D' domain of the modified VWF has the following sequence (SEQ ID NO:33).

SLSCRPPMVK LVCPAX$^1$NX$^2$RA EGLX$^3$CX$^4$KTCX$^5$ X$^6$YX$^7$LX$^8$CMSX$^9$G

CVSGCLCPPG MVRHX$^{10}$X$^{11}$RCVA LX$^{12}$RCPCFHQG KX$^{13}$YAX$^{14}$GETVK

IGCNTCVCRX$^{15}$ RKWNCTDHVC DA

The modified D' domain in the polypeptide of the present invention may have an amino acid sequence in accordance with one of the embodiments in the following table 2. Each line with an "embodiment No." represents an embodiment, wherein the D' domain in the polypeptide of the present invention has the amino acid sequence as shown in SEQ ID NO:33 with X$^1$ through X$^{15}$ having the indicated meanings. "neut" means a neutral amino acid.

TABLE 2

| Embodiment No. | $X^1$ | $X^2$ | $X^3$ | $X^4$ | $X^5$ | $X^6$ | $X^7$ | $X^8$ | $X^9$ | $X^{10}$ | $X^{11}$ | $X^{12}$ | $X^{13}$ | $X^{14}$ | $X^{15}$ |
|---|---|---|---|---|---|---|---|---|---|---|---|---|---|---|---|
| Wild type (SEQ ID NO: 31) | D | L | E | T | Q | N | D | E | M | E | N | E | E | P | D |
| 1.1 (SEQ ID NO: 33) | neut | L | E | T | Q | N | D | E | M | E | N | E | E | P | D |
| 1.2 (SEQ ID NO: 33) | K | L | E | T | Q | N | D | E | M | E | N | E | E | P | D |
| 1.3 (SEQ ID NO: 33) | R | L | E | T | Q | N | D | E | M | E | N | E | E | P | D |
| 2.1 (SEQ ID NO: 33) | D | P | E | T | Q | N | D | E | M | E | N | E | E | P | D |
| 3.1 (SEQ ID NO: 33) | D | L | neut | T | Q | N | D | E | M | E | N | E | E | P | D |
| 3.2 (SEQ ID NO: 33) | D | L | K | T | Q | N | D | E | M | E | N | E | E | P | D |
| 3.3 (SEQ ID NO: 33) | D | L | R | T | Q | N | D | E | M | E | N | E | E | P | D |
| 4.1 (SEQ ID NO: 33) | D | L | E | A | Q | N | D | E | M | E | N | E | E | P | D |
| 4.2 (SEQ ID NO: 33) | D | L | E | G | Q | N | D | E | M | E | N | E | E | P | D |
| 4.3 (SEQ ID NO: 33) | D | L | E | S | Q | N | D | E | M | E | N | E | E | P | D |
| 4.4 (SEQ ID NO: 33) | D | L | E | V | Q | N | D | E | M | E | N | E | E | P | D |
| 5.1 (SEQ ID NO: 33) | D | L | E | T | K | N | D | E | M | E | N | E | E | P | D |
| 5.2 (SEQ ID NO: 33) | D | L | E | T | R | N | D | E | M | E | N | E | E | P | D |
| 6.1 (SEQ ID NO: 33) | D | L | E | T | Q | K | D | E | M | E | N | E | E | P | D |
| 6.2 (SEQ ID NO: 33) | D | L | E | T | Q | R | D | E | M | E | N | E | E | P | D |
| 7.1 (SEQ ID NO: 33) | D | L | E | T | Q | N | neut | E | M | E | N | E | E | P | D |
| 7.2 (SEQ ID NO: 33) | D | L | E | T | Q | N | K | E | M | E | N | E | E | P | D |
| 7.3 (SEQ ID NO: 33) | D | L | E | T | Q | N | R | E | M | E | N | E | E | P | D |
| 8.1 (SEQ ID NO: 33) | D | L | E | T | Q | N | D | neut | M | E | N | E | E | P | D |
| 8.2 (SEQ ID NO: 33) | D | L | E | T | Q | N | D | K | M | E | N | E | E | P | D |
| 8.3 (SEQ ID NO: 33) | D | L | E | T | Q | N | D | R | M | E | N | E | E | P | D |
| 9.1 (SEQ ID NO: 33) | D | L | E | T | Q | N | D | E | K | E | N | E | E | P | D |
| 9.2 (SEQ ID NO: 33) | D | L | E | T | Q | N | D | E | R | E | N | E | E | P | D |
| 10.1 (SEQ ID NO: 33) | D | L | E | T | Q | N | D | E | M | neut | N | E | E | P | D |

TABLE 2-continued

| Embodiment No. | X¹ | X² | X³ | X⁴ | X⁵ | X⁶ | X⁷ | X⁸ | X⁹ | X¹⁰ | X¹¹ | X¹² | X¹³ | X¹⁴ | X¹⁵ |
|---|---|---|---|---|---|---|---|---|---|---|---|---|---|---|---|
| 10.2 (SEQ ID NO: 33) | D | L | E | T | Q | N | D | E | M | K | N | E | E | P | D |
| 10.3 (SEQ ID NO: 33) | D | L | E | T | Q | N | D | E | M | R | N | E | E | P | D |
| 11.1 (SEQ ID NO: 33) | D | L | E | T | Q | N | D | E | M | E | K | E | E | P | D |
| 11.2 (SEQ ID NO: 33) | D | L | E | T | Q | N | D | E | M | E | R | E | E | P | D |
| 12.1 (SEQ ID NO: 33) | D | L | E | T | Q | N | D | E | M | E | N | neut | E | P | D |
| 12.2 (SEQ ID NO: 33) | D | L | E | T | Q | N | D | E | M | E | N | K | E | P | D |
| 12.3 (SEQ ID NO: 33) | D | L | E | T | Q | N | D | E | M | E | N | R | E | P | D |
| 13.1 (SEQ ID NO: 33) | D | L | E | T | Q | N | D | E | M | E | N | E | neut | P | D |
| 13.2 (SEQ ID NO: 33) | D | L | E | T | Q | N | D | E | M | E | N | E | K | P | D |
| 13.3 (SEQ ID NO: 33) | D | L | E | T | Q | N | D | E | M | E | N | E | R | P | D |
| 14.1 (SEQ ID NO: 33) | D | L | E | T | Q | N | D | E | M | E | N | E | E | K | D |
| 14.2 (SEQ ID NO: 33) | D | L | E | T | Q | N | D | E | M | E | N | E | E | R | D |
| 15.1 (SEQ ID NO: 33) | D | L | E | T | Q | N | D | E | M | E | N | E | E | P | neut |
| 15.2 (SEQ ID NO: 33) | D | L | E | T | Q | N | D | E | M | E | N | E | E | P | K |
| 15.3 (SEQ ID NO: 33) | D | L | E | T | Q | N | D | E | M | E | N | E | E | P | R |

Embodiments 2.1 and 4.1-4.4 of table 2 are in accordance with the evolutionary approach, all other embodiments are in accordance with the electrostatic approach.

The amino acid positions which are preferably mutated in the modified VWF are selected from the group consisting of amino acid positions 779, 781, 787, 793, 794, 796, 798, 802, 818, 819, 825, 835, 838 and 853, wherein the numbering refers to the amino acid sequence shown in SEQ ID NO:2. That is, the D' domain of the modified VWF preferably has an amino acid substitution at one of positions 16, 18, 26, 30, 31, 39, 55, 56, 72, 75 or 90 of SEQ ID NO:31.

Preferably, the amino acid substitution in the modified VWF is at one of positions 789, 802, 818, 819 or 853 of the amino acid sequence as shown in SEQ ID NO:2. That is, the D' domain of the modified VWF preferably has one or more mutations at positions 39, 55, 56 and 90 of SEQ ID NO:31.

According to this invention the binding affinity of the polypeptide of the present invention to FVIII is higher than that of a reference polypeptide which has the same amino acid sequence except for the mutation in the D' domain.

The binding affinity of a VWF molecule to a Factor VIII molecule can be determined by a binding assay used in the art. For example, the VWF molecule may be immobilized on a solid support, increasing concentrations of Factor VIII are applied, incubated for a certain period of time, and after washing, bound Factor VIII is determined with a chromogenic assay. The affinity constant or dissociation constant may then be determined by Scatchard analysis or another suitable method. A method of determining the affinity of binding of human Factor VIII to von Willebrand Factor are described in Vlot et al. (1995), Blood, Volume 85, Number 11, 3150-3157. Preferably, however, the affinity of VWF to Factor VIII is determined as described in Example 4 of this application.

Any indication herein of affinity, including dissociation constants, preferably refers to the binding of the modified VWF of the invention, or of the polypeptide of the invention, to single chain FVIII represented by the amino acid sequence as shown in SEQ ID NO:37.

The dissociation constant of the complex consisting of VWF and FVIII is preferably 0.2 nmol/L or less, more preferably 0.175 nmol/L or less, more preferably 0.15 nmol/L or less, more preferably 0.125 nmol/L or less, more preferably 0.1 nmol/L or less, more preferably 0.05 nmol/L or less, most preferably 0.01 nmol/L or less.

The dissociation constant $K_D$ of a complex of the polypeptide of the invention and the Factor VIII of SEQ ID NO:37 is typically less than 90% of the dissociation constant $K_D$ of a complex of the reference polypeptide (e.g. the polypeptide of SEQ ID NO:32) and the Factor VIII of SEQ ID NO:37. The dissociation constant $K_D$ of a complex of the polypeptide of the invention and the Factor VIII of SEQ ID NO:37 is preferably less than 75%, more preferably less than 50%, more preferably less than 25%, more preferably less than 10%, more preferably less than 5%, of the dissociation constant $K_D$ of a complex of the reference polypeptide (e.g. the polypeptide of SEQ ID NO:32) and the Factor VIII of SEQ ID NO:37.

The binding affinity of the polypeptide of the present invention comprising the modified VWF to Factor VIII exceeds that of the reference polypeptide by at least 10%, preferably by at least 20%, more preferably by at least 30%, most preferably by at least 50%, more preferably by at least 75%, more preferably by at least 100%, more preferably by at least 250%, more preferably by at least 500%, more preferably by at least 1000%, more preferably by at least 10000%, most preferably by at least 100000%.

It has been found that the affinity of the polypeptide of the invention to single chain Factor VIII (e.g. represented by SEQ ID NO:37) is higher than to heterodimeric "two-chain" Factor VIII (e.g. represented by SEQ ID NO:36). Therefore, the preferred Factor VIII molecule in the complex of the invention is a single chain Factor VIII, most preferably it is the polypeptide of SEQ ID NO:37.

The reference polypeptide is a polypeptide the amino acid sequence of which is identical to that of the polypeptide of the present invention except for the mutation within the D' domain of VWF. That is, the reference polypeptide preferably has an amino acid sequence identical to that of the polypeptide of the present invention, with the proviso that the D' domain in the reference polypeptide consists of the amino acid sequence as shown in SEQ ID NO:31. In other words, the only difference in sequence between the polypeptide of the invention and the reference polypeptide lies in the amino acid sequence of the D' domain. The reference polypeptide has preferably been prepared under the same conditions as the polypeptide of the invention.

The polypeptide of the present invention may consist of the modified VWF. In another embodiment, the polypeptide of the present invention comprises a further amino acid sequence, preferably a heterologous amino acid sequence. The heterologous amino acid sequence is typically not fused to VWF in nature.

The present invention is particularly useful in cases where a VWF variant is used having an improved half-life. This can be achieved for example by fusing VWF to human serum albumin. It has been found, however, that such fusion proteins may have a reduced affinity to FVIII as compared to wild type VWF. This includes the risk that a complex of VWF fusion protein and FVIII administered to a patient may dissociate rather quickly, and the FVIII dissociated from the complex would bind to endogenous VWF. The positive effect of the complexation between a VWF with an increased half-life and FVIII, namely that also the half-life of FVIII is increased, can thus be lost if the affinity between VWF fusion protein and FVIII is too low. This problem is addressed by improving the binding of VWF to FVIII in accordance with this invention. As VWF fusion proteins are particularly at risk of having a reduced FVIII affinity, the present invention is particularly applicable to VWF fusion proteins.

Therefore, in one embodiment, the polypeptide of the present invention comprises the modified VWF and a half-life enhancing protein (HLEP). Preferably, the HLEP is an albumin.

One or more HLEPs may be fused to the C-terminal part of VWF preferably as not to interfere with the binding capabilities of VWF for example to FVIII, platelets, heparin or collagen.

In one embodiment the modified VWF has the following structure:

N-VWF-C-L1-H, [formula 1]

wherein
N is an N-terminal part of VWF,
L1 is a chemical bond or a linker sequence
H is a HLEP, and
C is a C-terminal part of VWF L1 may be a chemical bond or a linker sequence consisting of one or more amino acids, e.g. of 1 to 50, 1 to 30, 1 to 20, 1 to 15, 1 to 10, 1 to 5 or 1 to 3 (e.g. 1, 2 or 3) amino acids and which may be equal or different from each other. Usually, the linker sequences are not present at the corresponding position in the wild-type coagulation factor. Examples of suitable amino acids present in L1 include Gly and Ser.

Preferred HLEP sequences are described infra. Likewise encompassed by the invention are fusions to the exact "N-terminal amino acid" of the respective HLEP, or fusions to the "N-terminal part" of the respective HLEP, which includes N-terminal deletions of one or more amino acids of the HLEP.

The modified VWF or the complex of the FVIII with the modified VWF of the invention may comprise more than one HLEP sequence, e.g. two or three HLEP sequences. These multiple HLEP sequences may be fused to the C-terminal part of VWF in tandem, e.g. as successive repeats.

Linker Sequences

According to this invention, the therapeutic polypeptide moiety may be coupled to the HLEP moiety by a peptide linker. The linker should be non-immunogenic and may be a non-cleavable or cleavable linker.

Non-cleavable linkers may be comprised of alternating glycine and serine residues as exemplified in WO2007/090584.

In another embodiment of the invention the peptidic linker between the FVIII and/or the VWF moiety and the albumin moiety consists of peptide sequences, which serve as natural interdomain linkers in human proteins. Preferably such peptide sequences in their natural environment are located close to the protein surface and are accessible to the immune system so that one can assume a natural tolerance against this sequence. Examples are given in WO2007/090584.

Cleavable linkers should be flexible enough to allow cleavage by proteases. In a preferred embodiment the cleavage of the linker proceeds comparably fast as the activation of FVIII within the fusion protein, if the fusion protein is a modified FVIII.

The cleavable linker preferably comprises a sequence derived from
a) the therapeutic polypeptide to be administered itself if it contains proteolytic cleavage sites that are proteolytically cleaved during activation of the therapeutic polypeptide,
b) a substrate polypeptide cleaved by a protease which is activated or formed by the involvement of the therapeutic polypeptide.
c) a polypeptide involved in coagulation or fibrinolysis The linker region in a more preferred embodiment comprises a sequence of FVIII and/or VWF, which should result in a decreased risk of neoantigenic properties of the expressed fusion protein. Also in case the therapeutic protein is FVIII which needs to be proteolytically activated, the kinetics of the peptide linker cleavage will more closely reflect the coagulation-related activation kinetics of the zymogen.

The linker peptides are preferably cleavable by the proteases of the coagulation system, for example FIIa, FIXa, FXa, FXIa, FXIIa and FVIIa.

Exemplary combinations of therapeutic polypeptide, cleavable linker and HLEP include the constructs listed in WO2007/090584 (for example in table 2 and figure 4) and WO2007/144173 (for example in table 3a and 3b), but are not limited to these.

Half-Life Enhancing Polypeptides (HLEPs)

A "half-life enhancing polypeptide" as used herein is selected from the group consisting of albumin, a member of the albumin-family, the constant region of immunoglobulin G and fragments thereof, region and polypeptides capable of binding under physiological conditions to albumin, to members of the albumin family as well as to portions of an immunoglobulin constant region. It may be a full-length half-life-enhancing protein described herein (e.g. albumin, a member of the albumin-family or the constant region of immunoglobulin G) or one or more fragments thereof that are capable of stabilizing or prolonging the therapeutic activity or the biological activity of the coagulation factor. Such fragments may be of 10 or more amino acids in length or may include at least about 15, at least about 20, at least about 25, at least about 30, at least about 50, at least about 100, or more contiguous amino acids from the HLEP sequence or may include part or all of specific domains of the respective HLEP, as long as the HLEP fragment provides a functional half-life extension of at least 25% compared to a wild-type VWF.

The HLEP portion of the proposed coagulation factor insertion constructs of the invention may be a variant of a normal HLEP. The term "variants" includes insertions, deletions and substitutions, either conservative or non-conservative, where such changes do not substantially alter the active site, or active domain which confers the biological activities of the modified VWF.

In particular, the proposed VWF HLEP fusion constructs of the invention may include naturally occurring polymorphic variants of HLEPs and fragments of HLEPs. The HLEP may be derived from any vertebrate, especially any mammal, for example human, monkey, cow, sheep, or pig. Non-mammalian HLEPs include, but are not limited to, hen and salmon.

Albumin as HLEP

The terms, "human serum albumin" (HSA) and "human albumin" (HA) and "albumin" (ALB) are used interchangeably in this application. The terms "albumin" and "serum albumin" are broader, and encompass human serum albumin (and fragments and variants thereof) as well as albumin from other species (and fragments and variants thereof).

As used herein, "albumin" refers collectively to albumin polypeptide or amino acid sequence, or an albumin fragment or variant, having one or more functional activities (e.g., biological activities) of albumin. In particular, "albumin" refers to human albumin or fragments thereof, especially the mature form of human albumin as shown in SEQ ID NO:38 herein or albumin from other vertebrates or fragments thereof, or analogs or variants of these molecules or fragments thereof.

In particular, the proposed VWF fusion constructs of the invention may include naturally occurring polymorphic variants of human albumin and fragments of human albumin. Generally speaking, an albumin fragment or variant will be at least 10, preferably at least 40, most preferably more than 70 amino acids long. The albumin variant may preferentially consist of or alternatively comprise at least one whole domain of albumin or fragments of said domains, for example domains 1 (amino acids 1-194 of SEQ ID NO:38), 2 (amino acids 195-387 of SEQ ID NO: 38), 3 (amino acids 388-585 of SEQ ID NO: 38), 1+2 (1-387 of SEQ ID NO: 38), 2+3 (195-585 of SEQ ID NO: 38) or 1+3 (amino acids 1-194 of SEQ ID NO: 38+amino acids 388-585 of SEQ ID NO: 38). Each domain is itself made up of two homologous subdomains namely 1-105, 120-194, 195-291, 316-387, 388-491 and 512-585, with flexible inter-subdomain linker regions comprising residues Lys106 to Glu119, Glu292 to Val315 and Glu492 to Ala511.

The albumin portion of the proposed VWF fusion constructs of the invention may comprise at least one subdomain or domain of HA or conservative modifications thereof.

In a preferred embodiment the N-terminus of albumin is fused to the C-terminus of the amino acid sequence of the modified VWF. That is, the polypeptide of the present invention may have the structure:

N-mVWF-C-L1-A, wherein N is an N-terminal part of VWF, mVWF is the modified VWF as described hereinabove, C is a C-terminal part of VWF, L1 is a chemical bond or a linker sequence and A is albumin as defined hereinabove.

Immunoglobulins as HLEPs

Immunoglobulin G (IgG) constant regions (Fc) are known in the art to increase the half-life of therapeutic proteins (Dumont J A et al. 2006. BioDrugs 20:151-160). The IgG constant region of the heavy chain consists of 3 domains (CH1-CH3) and a hinge region. The immunoglobulin sequence may be derived from any mammal, or from subclasses IgG1, IgG2, IgG3 or IgG4, respectively. IgG and IgG fragments without an antigen-binding domain may also be used as HLEPs. The therapeutic polypeptide portion is connected to the IgG or the IgG fragments preferably via the hinge region of the antibody or a peptidic linker, which may even be cleavable. Several patents and patent applications describe the fusion of therapeutic proteins to immunoglobulin constant regions to enhance the therapeutic protein's in vivo half-lifes. US 2004/0087778 and WO 2005/001025 describe fusion proteins of Fc domains or at least portions of immunoglobulin constant regions with biologically active peptides that increase the half-life of the peptide, which otherwise would be quickly eliminated in vivo. Fc-IFN-β fusion proteins were described that achieved enhanced biological activity, prolonged circulating half-life and greater solubility (WO 2006/000448). Fc-EPO proteins with a prolonged serum half-life and increased in vivo potency were disclosed (WO 2005/063808) as well as Fc fusions with G-CSF (WO 2003/076567), glucagon-like peptide-1 (WO 2005/000892), clotting factors (WO 2004/101740) and interleukin-10 (U.S. Pat. No. 6,403,077), all with half-life enhancing properties.

In another embodiment, the functional half-life of polypeptide of the invention or of FVIII complexed with the polypeptide of the invention is prolonged compared to that of wild type VWF or to that of FVIII complexed with wild type VWF, or with the reference polypeptide as defined supra. The increase may be more than 15%, for example at least 20% or at least 50%. Again, such functional half-life values can be measured in vitro in blood samples taken at different time intervals from said mammal after the modified VWF or the complex of FVIII with modified VWF has been administered.

In another embodiment of the invention, the polypeptide of the invention or FVIII complexed with the polypeptide of the invention exhibits an improved in vivo recovery compared to wild type VWF or to FVIII complexed with wild type VWF, or with the reference polypeptide defined supra. The in vivo recovery can be determined in vivo for example in normal animals or in animal models of hemophilia A, like FVIII knockout mice in which one would expect an increased percentage of FVIII be found by antigen or activity assays in the circulation shortly (5 to 10 min.) after i.v. administration compared to the corresponding wild-type VWF, or reference polypeptide defined supra.

The in vivo recovery is preferably increased by at least 10%, more preferably by at least 20%, and even more preferably by at least 40% compared to FVIII complexed with wild-type VWF, or with the reference polypeptide defined supra.

In yet another embodiment of the invention immunoglobulin constant regions or portions thereof are used as HLEPs. Preferably the Fc region comprised of a CH2 and CH3 domain and a hinge region of an IgG, more preferably of an IgG1 or fragments or variants thereof are used, variants including mutations which enhance binding to the neonatal Fc receptor (FcRn).

Polynucleotides

The invention further relates to a polynucleotide encoding a modified VWF or a polypeptide comprising said modified VWF, as described in this application. The term "polynucleotide(s)" generally refers to any polyribonucleotide or polydeoxyribonucleotide that may be unmodified RNA or DNA or modified RNA or DNA. The polynucleotide may be single- or double-stranded DNA, single or double-stranded RNA. As used herein, the term "polynucleotide(s)" also includes DNAs or RNAs that comprise one or more modified bases and/or unusual bases, such as inosine. It will be appreciated that a variety of modifications may be made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells.

The skilled person will understand that, due to the degeneracy of the genetic code, a given polypeptide can be encoded by different polynucleotides. These "variants" are encompassed by this invention.

Preferably, the polynucleotide of the invention is an isolated polynucleotide. The term "isolated" polynucleotide refers to a polynucleotide that is substantially free from other nucleic acid sequences, such as and not limited to other chromosomal and extrachromosomal DNA and RNA. Isolated polynucleotides may be purified from a host cell. Conventional nucleic acid purification methods known to skilled artisans may be used to obtain isolated polynucleotides. The term also includes recombinant polynucleotides and chemically synthesized polynucleotides.

The invention further relates to a group of polynucleotides which together encode the modified VWF of the invention, or the polypeptide of the invention comprising the modified VWF. A first polynucleotide in the group may encode the N-terminal part of the modified VWF, and a second polynucleotide may encode the C-terminal part of the modified VWF.

Yet another aspect of the invention is a plasmid or vector comprising a polynucleotide according to the invention. Preferably, the plasmid or vector is an expression vector. In a particular embodiment, the vector is a transfer vector for use in human gene therapy.

The invention also relates to a group of plasmids or vectors that comprise the above group of polynucleotides. A first plasmid or vector may contain said first polynucleotide, and a second plasmid or vector may contain said second polynucleotide. Alternatively, both coding sequences are cloned into one expression vector either using two separate promoter sequences or one promoter and an internal ribosome entry site (IRES) element which may be used for example to direct the expression furin to enhance the generation of mature VWF.

Still another aspect of the invention is a host cell comprising a polynucleotide, a plasmid or vector of the invention, or a group of polynucleotides or a group of plasmids or vectors as described herein.

The host cells of the invention may be employed in a method of producing a modified VWF or a polypeptide comprising said modified VWF, which is part of this invention. The method comprises:
(a) culturing host cells of the invention under conditions such that the desired modified protein is expressed; and
(b) optionally recovering the desired modified protein from the host cells or from the culture medium.

It is preferred to purify the modified VWF of the present invention, or the polypeptide comprising the modified VWF to ≥80% purity, more preferably ≥95% purity, and particularly preferred is a pharmaceutically pure state that is greater than 99.9% pure with respect to contaminating macromolecules, particularly other proteins and nucleic acids, and free of infectious and pyrogenic agents. Preferably, an isolated or purified modified modified VWF of the invention or polypeptide of the invention is substantially free of other, non-related polypeptides.

The various products of the invention are useful as medicaments. Accordingly, the invention relates to a pharmaceutical composition comprising a modified VWF or a polypeptide comprising said modified VWF as described herein, a polynucleotide of the invention, or a plasmid or vector of the invention.

The invention also concerns a method of treating an individual suffering from a blood coagulation disorder such as hemophilia A or B or VWD. The method comprises administering to said individual an efficient amount of (i) FVIII and of the modified VWF or the polypeptide comprising the modified VWF or (ii) of the complex of FVIII with modified VWF or (iii) of the complex of FVIII with the polypeptide comprising modified VWF as described herein. In another embodiment, the method comprises administering to the individual an efficient amount of a polynucleotide of the invention or of a plasmid or vector of the invention. Alternatively, the method may comprise administering to the individual an efficient amount of the host cells of the invention described herein.

Expression of the Proposed Mutants

The production of recombinant mutant proteins at high levels in suitable host cells requires the assembly of the above-mentioned modified cDNAs into efficient transcriptional units together with suitable regulatory elements in a recombinant expression vector that can be propagated in various expression systems according to methods known to those skilled in the art. Efficient transcriptional regulatory elements could be derived from viruses having animal cells as their natural hosts or from the chromosomal DNA of animal cells. Preferably, promoter-enhancer combinations derived from the Simian Virus 40, adenovirus, BK polyoma virus, human cytomegalovirus, or the long terminal repeat of Rous sarcoma virus, or promoter-enhancer combinations including strongly constitutively transcribed genes in animal cells like beta-actin or GRP78 can be used. In order to achieve stable high levels of mRNA transcribed from the cDNAs, the transcriptional unit should contain in its 3'-proximal part a DNA region encoding a transcriptional termination-polyadenylation sequence. Preferably, this sequence is derived from the Simian Virus 40 early transcriptional region, the rabbit beta-globin gene, or the human tissue plasminogen activator gene.

The cDNAs are then integrated into the genome of a suitable host cell line for expression of the modified FVIII and/or VWF proteins. Preferably this cell line should be an animal cell-line of vertebrate origin in order to ensure correct folding, disulfide bond formation, asparagine-linked glycosylation and other post-translational modifications as well as secretion into the cultivation medium. Examples on other post-translational modifications are tyrosine O-sulfation and proteolytic processing of the nascent polypeptide chain. Examples of cell lines that can be use are monkey COS-cells, mouse L-cells, mouse C127-cells, hamster BHK-21 cells, human embryonic kidney 293 cells, and hamster CHO-cells.

The recombinant expression vector encoding the corresponding cDNAs can be introduced into an animal cell line in several different ways. For instance, recombinant expression vectors can be created from vectors based on different animal viruses. Examples of these are vectors based on baculovirus, vaccinia virus, adenovirus, and preferably bovine papilloma virus.

The transcription units encoding the corresponding DNA's can also be introduced into animal cells together with another recombinant gene which may function as a dominant selectable marker in these cells in order to facilitate the isolation of specific cell clones which have integrated the recombinant DNA into their genome. Examples of this type of dominant selectable marker genes are Tn5 amino glycoside phosphotransferase, conferring resistance to geneticin (G418), hygromycin phosphotransferase, conferring resistance to hygromycin, and puromycin acetyl transferase, conferring resistance to puromycin. The recombinant expression vector encoding such a selectable marker can reside either on the same vector as the one encoding the cDNA of the desired protein, or it can be encoded on a separate vector which is simultaneously introduced and integrated to the genome of the host cell, frequently resulting in a tight physical linkage between the different transcription units.

Other types of selectable marker genes which can be used together with the cDNA of the desired protein are based on various transcription units encoding dihydrofolate reductase (dhfr). After introduction of this type of gene into cells lacking endogenous dhfr-activity, preferentially CHO-cells (DUKX-B11, DG-44), it will enable these to grow in media lacking nucleosides. An example of such a medium is Ham's F12 without hypoxanthine, thymidin, and glycine. These dhfr-genes can be introduced together with the FVIII cDNA transcriptional units into CHO-cells of the above type, either linked on the same vector or on different vectors, thus creating dhfr-positive cell lines producing recombinant protein.

If the above cell lines are grown in the presence of the cytotoxic dhfr-inhibitor methotrexate, new cell lines resistant to methotrexate will emerge. These cell lines may produce recombinant protein at an increased rate due to the amplified number of linked dhfr and the desired protein's transcriptional units. When propagating these cell lines in increasing concentrations of methotrexate (1-10000 nM), new cell lines can be obtained which produce the desired protein at very high rate.

The above cell lines producing the desired protein can be grown on a large scale, either in suspension culture or on various solid supports. Examples of these supports are micro carriers based on dextran or collagen matrices, or solid supports in the form of hollow fibres or various ceramic materials. When grown in cell suspension culture or on micro carriers the culture of the above cell lines can be performed either as a bath culture or as a perfusion culture with continuous production of conditioned medium over extended periods of time. Thus, according to the present invention, the above cell lines are well suited for the development of an industrial process for the production of the desired recombinant mutant proteins Purification and Formulation The recombinant modified VWF protein, which accumulates in the medium of secreting cells of the above types, can be concentrated and purified by a variety of biochemical and chromatographic methods, including methods utilizing differences in size, charge, hydrophobicity, solubility, specific affinity, etc. between the desired protein and other substances in the cell cultivation medium.

An example of such purification is the adsorption of the recombinant mutant protein to a monoclonal antibody, directed to e.g. a HLEP, preferably human albumin, or directed to the respective coagulation factor, which is immobilised on a solid support. After adsorption of the modified VWF to the support, washing and desorption, the protein can be further purified by a variety of chromatographic techniques based on the above properties. The order of the purification steps is chosen e.g. according to capacity and selectivity of the steps, stability of the support or other aspects. Preferred purification steps e.g. are but are not limited to ion exchange chromatography steps, immune affinity chromatography steps, affinity chromatography steps, hydrophobic interaction chromatography steps, dye chromatography steps, hydroxyapatite chromatography steps, multimodal chromatography steps, and size exclusion chromatography steps.

In order to minimize the theoretical risk of virus contaminations, additional steps may be included in the process that allow effective inactivation or elimination of viruses. Such steps e.g. are heat treatment in the liquid or solid state, treatment with solvents and/or detergents, radiation in the visible or UV spectrum, gamma-radiation or nanofiltration.

The modified polynucleotides (e.g. DNA) of this invention may also be integrated into a transfer vector for use in the human gene therapy.

The various embodiments described herein may be combined with each other. The present invention will be further described in more detail in the following examples thereof. This description of specific embodiments of the invention will be made in conjunction with the appended figures.

The modified VWF as described in this invention can be formulated into pharmaceutical preparations for therapeutic use. The purified protein may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", 3$^{rd}$ edition, Kibbe et al., Pharmaceutical Press (2000)). Standard pharmaceutical formulation techniques are well known to persons skilled in the art (see, e.g., 2005 Physicians' Desk Reference®, Thomson Healthcare: Montvale, N.J., 2004; Remington: The Science and Practice of Pharmacy, 20th ed., Gennaro et al., Eds. Lippincott Williams & Wilkins: Philadelphia, Pa., 2000). In particular, the pharmaceutical composition comprising the polypeptide variant of the invention may be formulated in lyophilized or stable liquid form. The polypeptide variant may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of administration. Various delivery systems are known and can be used to administer the composition by any convenient route. Preferentially, the compositions of the invention are administered systemically. For systemic use, insertion proteins of the invention are formulated for parenteral (e.g. intravenous, subcutaneous, intramuscular, intraperitoneal, intracerebral, intrapulmonar, intranasal or transdermal) or enteral (e.g., oral, vaginal or rectal) delivery according to conventional methods. The most preferential routes of administration are intravenous and subcutaneous administration. The formulations can be administered continuously by infusion or by bolus injection. Some formulations encompass slow release systems.

The insertion proteins of the present invention are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, mode of administration and has to be determined in preclinical and clinical trials for each respective indication.

The pharmaceutical composition of the invention may be administered alone or in conjunction with other therapeutic agents. These agents may be incorporated as part of the same pharmaceutical. One example of such an agent is the combination of modified VWF with non-modified FVIII or the combination of modified VWF with modified FVIII.

Summary of the nucleotide and amino acid sequences referred to herein:

TABLE 3

| SEQ ID NO: | Description |
|---|---|
| 1 | nucleotide sequence of DNA encoding SEQ ID NO: 2 |
| 2 | amino acid sequence of human VWF pre-propolypeptide |
| 3-30 | nucleotide sequences of primers, see Examples |
| 31 | amino acid sequence of the D' domain of human VWF |
| 32 | amino acid sequence of mature human VWF |
| 33 | amino acid sequence of the D' domain of mutated human VWF with 15 potentially modified residues |
| 34 | amino acid sequence of the D' domain of mutated human VWF with 11 potentially modified residues |
| 35 | amino acid sequence of the D' domain of mutated human VWF with 11 potentially modified residues |
| 36 | amino acid sequence of human Factor VIII |
| 37 | amino acid sequence of a mature single-chain Factor VIII |
| 38 | amino acid sequence of human serum albumin |

EXAMPLES

Example 1

Generation of Expression Vectors for VWF Mutants

An expression plasmid based on pIRESpuro3 (Clontech) containing a full length VWF cDNA sequence in its multiple cloning site had been generated previously (pVWF-2448). The VWF cDNA sequence contained in this vector is displayed as SEQ ID NO:1, its corresponding protein sequence as SEQ ID NO:2.

For generating such expression vectors, the VWF cDNA may be amplified by polymerase chain reaction (PCR) using primer set VWF+ and VWF− (SEQ ID NO:3 and 4) under standard conditions known to those skilled in the art (and as described e.g. in Current Protocols in Molecular Biology, Ausubel F M et al. (eds.) John Wiley & Sons, Inc.) from a plasmid containing VWF cDNA (as obtainable commercially, e.g. pMT2-VWF from ATCC, No. 67122). The resulting PCR fragment may be digested by restriction endonuclease EcoRI and ligated into expression vector pIRESpuro3 (BD Biosciences, Franklin Lakes, N.J., USA) which had been linearized by EcoRI. The resulting expression plasmid will contain a wild-type cDNA of VWF downstream of the CMV promoter.

In order to introduce mutations in the VWF sequence site directed mutagenesis (QuickChange XL Site Directed Mutagenesis Kit, Stratagene, La Jolla, Calif., USA) was applied on plasmid pVWF-2448 according to the following protocol as suggested by the kit manufacturer. Per mutagenesis reaction 5 µl of 10× reaction buffer, 1 µl of plasmid DNA pVWF-2448 (50 ng), 1 µl (10 pmol/µl) each of the respective two mutagenesis oligonucleotides as outlined in table 4, 1 µl dNTP Mix, 3 µl Quick-Solution, 1 µl Turbo Polymerase (2.5 U/µl) and 37 µl H$_2$O were mixed and subjected to a polymerase chain reaction with an initial denaturation for 2 min at 95° C., 18 cycles of a) denaturation for 50 sec. at 95° C., b) annealing for 50 sec at 60° C. and c) elongation for 14 min at 68° C., followed by a single terminal elongation phase of 7 min at 68° C. Subsequently 1 µl of Dpnl enzyme from the kit was added and the reaction incubated for another 60 min at 37° C. After that 3 µl of the mutagenesis reaction were transformed into *E. coli*. Clones were isolated, plasmid DNA extracted and the mutations in the VWF sequences were verified by DNA sequencing.

The following table 4 lists the oligonucleotides used for mutagenesis, the respective mutations introduced and the designation of the resulting plasmids with the mutant VWF sequences.

TABLE 4

| SEQ ID NO: | Oligo-nucleotide | Mutagenesis oligonucleotide sequence (5'→3') | VWF mutation (from x to y) | Designation of expression plasmid |
|---|---|---|---|---|
| 5 | We4070 | GGTGTGTCCCGCTAA CAACCTGCGGGCTG | Asp 779 Asn | pIRES-2462 |
| 6 | We4071 | CAGCCCGCAGGTTGTT AGCGGGACACACC | | |
| 7 | We4072 | GTCCCGCTGACAACCC TCGGGCTGAAGGG | Leu 781 Pro | pIRES-2463 |
| 8 | We4073 | CCCTTCAGCCCGAGGG TTGTCAGCGGGAC | | |

TABLE 4-continued

| SEQ ID NO: | Oligo-nucleotide | Mutagenesis oligonucleotide sequence (5'→3') | VWF mutation (from x to y) | Designation of expression plasmid |
|---|---|---|---|---|
| 9 | We4074 | CTGAAGGGCTCGAGTGTG CCAAAACGTGCCAGAAC | Thr 789 Ala | pIRES-2464 |
| 10 | We4075 | GTTCTGGCACGTTTTGGC ACACTCGAGCCCTTCAG | | |
| 11 | We4076 | GTGTACCAAAACGTGCCG GAACTATGACCTGGAGTGC | Gln 793 Arg | pIRES-2465 |
| 12 | We4077 | GCACTCCAGGTCATAGTTC CGGCACGTTTTGGTACAC | | |
| 13 | We4078 | GTACCAAAACGTGCCAGAA GTATGACCTGGAGTGC | Asn 794 Lys | pIRES-2466 |
| 14 | We4079 | GCACTCCAGGTCATACT TCTGGCACGTTTTGGTAC | | |
| 15 | We4080 | CTGGAGTGCATGAGCAGG GGCTGTGTCTCTGGCTG | Met 802 Arg | pIRES-2467 |
| 16 | We4081 | CAGCCAGAGACACAGCC CCTGCTCATGCACTCCAG | | |
| 17 | We4082 | CTGGAGTGCATGAGCAA GGGCTGTGTCTCTGGCTG | Met 802 Lys | pIRES-2468 |
| 18 | We4083 | CAGCCAGAGACACAGCCC TTGCTCATGCACTCCAG | | |
| 19 | We4084 | CATGGTCCGGCATGCCAA CAGATGTGTGGCCCTG | Glu 818 Ala | pIRES-2469 |
| 20 | We4085 | CAGGGCCACACATCTGT TGGCATGCCGGACCATG | | |
| 21 | We4086 | CATGGTCCGGCATAAGAA CAGATGTGTGGCCCTG | Glu 818 Lys | pIRES-2470 |
| 22 | We4087 | CAGGGCCACACATCTGTT CTTATGCCGGACCATG | | |
| 23 | We4088 | GGTCCGGCATGAGAAGA GATGTGTGGCCCTG | Asn 819 Lys | pIRES-2471 |
| 24 | We4089 | CAGGGCCACACATCTCTT CTCATGCCGGACC | | |
| 25 | We4090 | GCTTCCATCAGGGCAAGCA GTATGCCCCTGGAGAAAC | Glu 835 Gln | pIRES-2472 |
| 26 | We4091 | GTTTCTCCAGGGGCATAC TGCTTGCCCTGATGGAAGC | | |
| 27 | We4092 | GGGCAAGGAGTATGCCAAG GGAGAAACAGTGAAGATTG | Pro 838 Lys | pIRES-2473 |
| 28 | We4093 | CCAATCTTCACTGTTTCTCC CTTGGCATACTCCTTGCCC | | |
| 29 | We4094 | CGGAACCGGAAGTGGAACT GCACAGACCATGTGTG | Asp 853 Asn | pIRES-2474 |
| 30 | We4095 | CACACATGGTCTGTGCAG TTCCACTTCCGGTTCCG | | |

Using the protocols and plasmids described above and by applying molecular biology techniques known to those skilled in the art (and as described e.g. in Current Protocols in Molecular Biology, ibid) other constructs can be made by the artisan for mutation of other amino acid residues.

Example 2

Transfection of Plasmids and Expression of VWF Mutants in HEK-293 Cells

Expression plasmids were grown up in *E. coli* TOP10 (Invitrogen, Carlsbad, Calif., USA) and purified using standard protocols (Qiagen, Hilden, Germany). HEK-293 cells were transfected using the Lipofectamine 2000 reagent (Invitrogen) and grown up in serum-free medium (Invitrogen 293 Express) in the presence of 4 µg/ml Puromycin. Transfected cell populations were spread through T-flasks into shake flasks from which supernatants were harvested for VWF antigen quantitation and Biacore analysis.

Example 3

Quantitation of VWF Antigen

VWF antigen in culture supernatant was determined by an ELISA whose performance is known to those skilled in the art. Briefly, microplates were incubated with 100 µL per well of the capture antibody (rabbit anti human vWF-IgG, Dako A0082 [Dako, Hamburg, Germany], diluted 1:2000 in buffer A [Sigma C3041, Sigma-Aldrich, Munich, Germany]) overnight at ambient temperature. After washing plates three times with buffer B (Sigma P3563), each well was incubated with 200 µL buffer C (Sigma P3688) for 1.5 hours at ambient temperature (blocking). After another three wash steps with buffer B, serial dilutions of the test sample in buffer B as well as serial dilutions of standard human plasma (ORKL21; 20-0.2 mU/mL; Siemens Healthcare Diagnostics, Marburg, Germany) in buffer B (volumes per well: 100 µL) were incubated for 1.5 hours at ambient temperature. After three wash steps with buffer B, 100 µL of a 1:16000 dilution in buffer B of the detection antibody (rabbit anti human vWF-IgG, Dako P0226, peroxidase labelled) were added to each well and incubated for 1 hour at ambient temperature. After three wash steps with buffer B, 100 µL of substrate solution (OUVF, Siemens Healthcare Diagnostics) were added per well and incubated for 30 minutes at ambient temperature in the dark. Addition of 100 µL undiluted stop dilution (OSFA, Siemens Healthcare Diagnostics) prepared the samples for reading in a suitable microplate reader at 450 nm wavelength. Concentrations of the test samples were then calculated using the standard curve with standard human plasma as reference.

Example 4

Analysis of the Binding of VWF Mutants to FVIII

All binding tests are performed using a Biacore 3000 instrument (GE Healthcare) and CM 3 chips. System buffer and dilution buffer for FVIII products is HBS-P (20 mmol/L Hepes, 100 mmol/L NaCl, 0.005% polysorbate 20, pH 7.3). A monoclonal anti-vWF antibody not interfering with FVIII binding is immobilized by using Biacore amino coupling chemistry. All immobilization, saturation and binding assays are performed at a controlled temperature of 25° C.

Monoclonal anti-vWF antibody is covalently bound to an activated CM 3 chip by NHS and EDC (both from GE Healthcare), a coupling where the antibody is fixed at its aminoterminus to the dextran filaments on the gold surface of the chip. For immobilization the monoclonal antibody is diluted to 10 µg/mL in 10 mM sodium acetate (pH 4.5). The antibody solution is flown over the chip for 8 min at a flowrate of 5 µL/min.

After the immobilization procedure non-coupled dextran filaments are saturated by flowing 1M ethanolamine (pH 8.3) over the chip for 5 min (at a flow rate of 5 µL/min). A reference flow cell is set up by saturating an empty flow cell with ethanolamine by using the same procedure as above.

VWF mutants are immobilized to the covalently coupled anti VWF monoclonal antibody by flowing VWF mutants (in culture supernatant) over the chip until its saturation at a flow rate of 5 µL/min.

For evaluation of the binding of VWF mutants to FVIII, a FVIII preparation is serially diluted in HBS-P buffer, e.g.

to concentrations 0.3125 μg/mL, 0.625 μg/mL, 1.25 μg/mL, 2.5 μg/mL and 5 μg/mL. A sample of each dilution is flown over the chip for 12 min (flow rate 10 μL/min.), followed by a dissociation time of 5 min with HBS-P buffer. After each run the chip is washed with 250 mM $CaCl_2$ for 3 min. to elute FVIII bound to VWF. Thereafter the VWF mutant is stripped by washing with 10 mM glycine (pH 2.1) for 4 min and a the next VWF mutant is bound to the chip as described above.

Binding parameters are calculated using BIAevaluation Software (Biacore, GE Healthcare). The curve fitting methods are based on Langmuir equations. The input data for calculations are the molar masses of the analytes, other parameters like max. RU and slopes are automatically extracted out of the fitted association and dissociation curves. The outputs of Biaevaluation Software are the association rate constants and the dissociation rate constants, from which the affinity constants are calculated.

The invention claimed is:

1. A polypeptide comprising a modified von Willebrand Factor (VWF),
   wherein the amino acid sequence of the modified VWF is identical to a human VWF sequence except for a modified D' domain, wherein the modified D' domain has at least one mutation relative to the amino acid sequence of positions 764 to 865 of SEQ ID NO:2,
   wherein the at least one mutation within the D' domain comprises at least one amino acid substitution at a position selected from the group consisting of 779, 781, 793, 794, 796, 798, 802, 818, 819, 825, 835, 838 and 853 of the VWF amino acid sequence as shown in SEQ ID NO:2,
   and wherein the binding affinity of the polypeptide comprising the modified VWF to Factor VIII (FVIII) is higher than that of a reference human VWF polypeptide, wherein the amino acid sequence of the reference polypeptide comprises positions 764 to 865 of SEQ ID NO:2.

2. The polypeptide of claim 1, wherein the amino acid substitution within the D' domain is selected from the group consisting of Asp779Asn, Leu781Pro, Gln793Arg, Asn794Lys, Met802Arg, Met802Lys, Glu818Ala, Glu818Lys, Asn819Lys, Glu835Gln, Pro838Lys, and Asp853Asn, wherein the amino acid numbering refers to SEQ ID NO:2.

3. The polypeptide of claim 1, further comprising a half-life enhancing protein (HLEP).

4. The polypeptide of claim 3, wherein said HLEP is an albumin.

5. The polypeptide of claim 4, wherein the N-terminus of the albumin is fused to the C-terminus of the modified VWF amino acid sequence.

6. A pharmaceutical composition comprising the polypeptide of claim 1.

7. A complex comprising a Factor VIII molecule and the polypeptide of claim 1.

8. The complex of claim 7 wherein the Factor VIII molecule comprises the polypeptide of SEQ ID NO:37, and wherein the dissociation constant $K_D$ of the complex is less than 90% of the dissociation constant $K_D$ of a complex of the reference polypeptide and the Factor VIII molecule of SEQ ID NO:37, wherein the amino acid sequence of the reference polypeptide comprises positions 764 to 865 of SEQ ID NO:2.

9. A method of treating a bleeding disorder, comprising administering to a patient in need thereof a pharmaceutically effective amount of the polypeptide of claim 1.

10. The method of claim 9, wherein the bleeding disorder is von Willebrand's disease (VWD) or hemophilia A.

11. A method of increasing the Factor VIII binding affinity of VWF, comprising modifying a human VWF in a D' domain, wherein the modified D' domain has at least one mutation relative to the amino acid sequence of positions 764 to 865 of SEQ ID NO:2, wherein the at least one mutation within the D' domain comprises at least one amino acid substitution at a position selected from the group consisting of 779, 781, 793, 794, 796, 798, 802, 818, 819, 825, 835, 838 and 853 of the VWF amino acid sequence as shown in SEQ ID NO:2, and wherein the binding affinity of the polypeptide comprising the modified VWF to Factor VIII (FVIII) is higher than that of a reference human VWF polypeptide, wherein the amino acid sequence of the reference polypeptide comprises positions 764 to 865 of SEQ ID NO:2.

12. The method of claim 11, wherein at least one acidic residue of the VWF D' domain is replaced with a neutral or basic amino acid, or wherein at least one neutral residue of the VWF D' domain is replaced with a basic amino acid.

13. A method for increasing the half-life of Factor VIII, comprising mixing the Factor VIII with the modified VWF polypeptide of claim 1.

14. The method of claim 13, wherein said modified VWF polypeptide further comprises a half-life enhancing protein (HLEP).

15. A method of preparing a complex comprising FVIII and a modified VWF, comprising mixing a Factor VIII polypeptide with the polypeptide of claim 1.

16. A polynucleotide encoding the polypeptide of claim 1.

17. A plasmid or vector comprising the polynucleotide of claim 16.

18. The plasmid or vector of claim 17, said plasmid or vector being an expression vector.

19. A host cell comprising the polynucleotide of claim 16.

20. A method of producing a modified VWF, comprising:
(a) culturing the host cell of claim 19 under conditions such that the modified VWF is expressed; and
(b) optionally recovering the modified VWF from the host cells or from the culture medium.

* * * * *

SEQUENCE LISTING

```
<160> NUMBER OF SEQ ID NOS: 38

<210> SEQ ID NO 1
<211> LENGTH: 8442
<212> TYPE: DNA
<213> ORGANISM: Homo sapiens

<400> SEQUENCE: 1
atgattcctg ccagatttgc cggggtgctg cttgctctgg ccctcatttt gccagggacc      60
ctttgtgcag aaggaactcg cggcaggtca tccacggccc gatgcagcct tttcggaagt     120
gacttcgtca acacctttga tgggagcatg tacagctttg cgggatactg cagttacctc     180
ctggcagggg gctgccagaa acgctccttc tcgattattg gggacttcca gaatggcaag     240
agagtgagcc tctccgtgta tcttggggaa ttttttgaca tccatttgtt tgtcaatggt     300
accgtgacac aggggggacca agagtctcc atgccctatg cctccaaagg ctgtatcta     360 gaaactgagg ctgggtacta caagctgtcc ggtgaggcct atggctttgt ggccaggatc     420
gatggcagcg gcaactttca agtcctgctg tcagacagat acttcaacaa gacctgcggg     480
ctgtgtggca actttaacat ctttgctgaa gatgacttta tgacccaaga agggaccttg     540
acctcggacc cttatgactt tgccaactca tgggctctga gcagtggaga cagtggtgt      600 gaacgggcat ctcctcccag cagctcatgc aacatctcct ctgggaaat gcagaagggc     660 ctgtgggagc agtgccagct tctgaagagc acctcggtgt tgcccgctg ccaccctctg     720 gtggaccccg agccttttgt ggccctgtgt gagaagactt tgtgtgagtg tgctgggggg     780
ctggagtgcg cctgccctgc cctcctggag tacgcccgga cctgtgccca ggagggaatg     840
gtgctgtacg gctggaccga ccacagcgcg tgcagcccag tgtgccctgc tggtatggag     900
tataggcagt gtgtgtcccc ttgcgccagg acctgccaga gcctgcacat caatgaaatg     960
tgtcaggagc gatgcgtgga tggctgcagc tgccctgagg acagctcct ggatgaaggc    1020 ctctgcgtgg agagccacga gtgtccctgc gtgcattccg gaaagcgcta ccctccggc    1080 acctccctct ctcgagactg caacacctgc atttgccgaa acagccagtg gatctgcagc    1140
aatgaagaat gtccagggga gtgccttgtc acaggtcaat cacacttcaa gagctttgac    1200
aacagatact tcaccttcag tgggatctgc cagtacctgc tggcccggga ttgccaggac    1260
cactccttct ccattgtcat tgagactgtc cagtgtgctg atgaccgcga cgctgtgtgc    1320
acccgctccg tcaccgtccg gctgcctggc ctgcacaaca gccttgtgaa actgaagcat    1380
ggggcaggag ttgccatgga tggccaggac gtccagctcc cctcctgaa aggtgacctc    1440 cgcatccagc atacagtgac ggcctccgtg cgcctcagct acgggggaga cctgcagatg    1500
gactgggatg gccgcgggag gctgctggtg aagctgtccc ccgtctatgc cgggaagacc    1560
tgcggcctgt gtgggaatta caatggcaac cagggcgacg acttccttac ccctctgggg    1620
```

```
ctggcggagc cccgggtgga ggacttcggg aacgcctgga agctgcacgg ggactgccag    1680
gacctgcaga agcagcacag cgatccctgc gccctcaacc cgcgcatgac caggttctcc    1740
gaggaggcgt gcgcggtcct gacgtccccc acattcgagg cctgccatcg tgccgtcagc    1800
ccgctgccct acctgcggaa ctgccgctac gacgtgtgct cctgctcgga cggccgcgag    1860
tgcctgtgcg gcgccctggc cagctatgcc gcggcctgcg cggggagagg cgtgcgcgtc    1920
gcgtggcgcg agccaggccg ctgtgagctg aactgcccga aggccaggt gtacctgcag     1980 tgcgggaccc cctgcaacct gacctgccgc tctctctctt acccggatga ggaatgcaat    2040
gaggcctgcc tggagggctg cttctgcccc ccagggctct acatggatga gggggggac    2100 tgcgtgccca aggcccagtg cccctgttac tatgacggtg agatcttcca gccagaagac    2160
atcttctcag accatcacac catgtgctac tgtgaggatg gcttcatgca ctgtaccatg    2220
agtggagtcc ccggaagctt gctgcctgac gctgtcctca gcagtcccct gtctcatcgc    2280
agcaaaagga gcctatcctg tcggcccccc atggtcaagc tggtgtgtcc cgctgacaac    2340
ctgcgggctg aagggctcga gtgtaccaaa acgtgccaga actatgacct ggagtgcatg    2400
agcatgggct gtgtctctgg ctgcctctgc ccccgggca tggtccggca tgagaacaga     2460
tgtgtggccc tggaaaggtg tccctgcttc catcagggca aggagtatgc ccctggagaa    2520
acagtgaaga ttggctgcaa cacttgtgtc tgtcgggacc ggaagtggaa ctgcacagac    2580
catgtgtgtg atgccacgtg ctccacgatc ggcatggccc actacctcac cttcgacggg    2640
ctcaaatacc tgttccccgg ggagtgccag tacgttctgg tgcaggatta ctgcggcagt    2700
aaccctggga cctttcggat cctagtgggg aataagggat gcagccaccc ctcagtgaaa    2760
tgcaagaaac gggtcaccat cctggtggag ggaggagaga ttgagctgtt tgacggggag    2820
gtgaatgtga agaggcccat gaaggatgag actcactttg aggtggtgga gtctggccgg    2880
tacatcattc tgctgctggg caaagccctc tccgtggtct gggaccgcca cctgagcatc    2940
tccgtggtcc tgaagcagac ataccaggag aaagtgtgtg gcctgtgtgg gaattttgat    3000
ggcatccaga caatgacctt caccagcagc aacctccaag tggaggaaga ccctgtggac    3060
tttgggaact cctggaaagt gagctcgcag tgtgctgaca ccagaaaagt gcctctggac    3120
tcatcccctg ccacctgcca taacaacatc atgaagcaga cgatggtgga ttcctcctgt    3180
agaatcctta ccagtgacgt cttccaggac tgcaacaagc tggtggaccc cgagccatat    3240
ctggatgtct gcatttacga cacctgctcc tgtgagtcca ttggggactg cgcctgcttc    3300
tgcgacacca ttgctgccta tgcccacgtg tgtgcccagc atggcaaggt ggtgacctgg    3360
aggacggcca cattgtgccc ccagagctgc gaggagagga tctccgggga gaacgggtat    3420
gagtgtgagt ggcgctataa cagctgtgca cctgcctgtc aagtcacgtg tcagcacccc    3480
gagccactgg cctgccctgt gcagtgtgtg gagggctgcc atgcccactg ccctccaggg    3540
aaaatcctgg atgagctttt gcagacctgc gttgaccctg aagactgtcc agtgtgtgag    3600
gtggctggcc ggcgttttgc ctcaggaaag aaagtcacct tgaatcccag tgaccctgag    3660
cactgccaga tttgccactg tgatgttgtc aacctcacct gtgaagcctg ccaggagccg    3720
ggaggcctgt tggtgcctcc cacagatgcc ccggtgagcc ccaccactct gtatgtggag    3780
gacatctcgg aaccgccgtt gcacgatttc tactgcagca ggctactgga cctggtcttc    3840
ctgctggatg ctcctccag gctgtccgag gctgagtttg aagtgctgaa ggcctttgtg    3900
gtggacatga tggagcggct gcgcatctcc cagaagtggg tccgcgtggc cgtggtggag    3960
taccacgacg gctcccacgc ctacatcggg ctcaaggacc ggaagcgacc gtcagagctg    4020
```

-continued

```
cggcgcattg ccagccaggt gaagtatgcg ggcagccagg tggcctccac cagcgaggtc    4080
ttgaaataca cactgttcca aatcttcagc aagatcgacc gccctgaagc ctcccgcatc    4140
gccctgctcc tgatggccag ccaggagccc aacggatgt cccggaactt tgtccgctac    4200
gtccagggcc tgaagaagaa gaaggtcatt gtgatcccgg tgggcattgg gccccatgcc    4260
aacctcaagc agatccgcct catcgagaag caggcccctg agaacaaggc cttcgtgctg    4320
agcagtgtgg atgagctgga gcagcaaagg gacgagatcg ttagctacct ctgtgacctt    4380
gcccctgaag ccctcctcc tactctgccc cccacatgg cacaagtcac tgtgggcccg    4440
gggctcttgg gggtttcgac cctggggccc aagaggaact ccatggttct ggatgtggcg    4500
ttcgtcctgg aaggatcgga caaaattggt gaagccgact tcaacaggag caaggagttc    4560
atggaggagg tgattcagcg gatggatgtg gccaggaca gcatccacgt cacggtgctg    4620
cagtactcct acatggtgac cgtggagtac cccttcagcg aggcacagtc caaaggggac    4680
atcctgcagc gggtgcgaga gatccgctac cagggcggca acaggaccaa cactgggctg    4740
gccctgcggt acctctctga ccacagcttc ttggtcagcc agggtgaccg ggagcaggcg    4800
cccaacctgg tctacatggt caccggaaat cctgcctctg atgagatcaa gaggctgcct    4860
ggagacatcc aggtggtgcc cattggagtg ggccctaatg ccaacgtgca ggagctggag    4920
aggattggct ggcccaatgc ccctatcctc atccaggact ttgagacgct ccccgagag    4980
gctcctgacc tggtgctgca gaggtgctgc tccggagagg ggctgcagat ccccacccctc    5040
tccctgcac ctgactgcag ccagcccctg gacgtgatcc ttctcctgga tggctcctcc    5100
agtttcccag cttcttattt tgatgaaatg aagagtttcg ccaaggcttt catttcaaaa    5160
gccaatatag ggcctcgtct cactcaggtg tcagtgctgc agtatggaag catcaccacc    5220
attgacgtgc catggaacgt ggtcccggag aaagcccatt gctgagcct tgtggacgtc    5280
atgcagcggg agggaggccc cagccaaatc ggggatgcct tgggctttgc tgtgcgatac    5340
ttgacttcag aaatgcatgg ggcgcgcccg ggagcctcaa aggcggtggt catcctggtc    5400
acggacgtct ctgtggattc agtggatgca gcagctgatg ccgccaggtc caacagagtg    5460
acagtgttcc ctattggaat tggagatcgc tacgatgcag cccagctacg atcttggca    5520
ggcccagcag gcgactccaa cgtggtgaag ctccagcgaa tcgaagacct ccctaccatg    5580
gtcaccttgg gcaattcctt cctccacaaa ctgtgctctg gatttgttag gatttgcatg    5640
gatgaggatg ggaatgagaa gaggcccggg gacgtctgga ccttgccaga ccagtgccac    5700
accgtgactt gccagccaga tggccagacc ttgctgaaga gtcatcgggt caactgtgac    5760
cgggggctga ggccttcgtg ccctaacagc cagtcccctg ttaaagtgga agagacctgt    5820
ggctgccgct ggacctgccc ctgcgtgtgc acaggcagct ccactcggca catcgtgacc    5880
tttgatgggc agaatttcaa gctgactggc agctgttctt atgtcctatt tcaaaacaag    5940
gagcaggacc tggaggtgat tctccataat ggtgcctgca gccctggagc aaggcagggc    6000
tgcatgaaat ccatcgaggt gaagcacagt gccctctccg tcgagctgca cagtgacatg    6060
gaggtgacgg tgaatgggag actggtctct gttccttacg tgggtgggaa catggaagtc    6120
aacgtttatg gtgccatcat gcatgaggtc agattcaatc accttggtca catcttcaca    6180
ttcactccac aaaacaatga gttccaactg cagctcagcc caagacttt tgcttcaaag    6240
acgtatggtc tgtgtgggat ctgtgatgag aacggagcca atgacttcat gctgagggat    6300
ggcacagtca ccacagactg gaaaacactt gttcaggaat ggactgtgca gcggccaggg    6360
```

```
cagacgtgcc agcccatcct ggaggagcag tgtcttgtcc ccgacagctc ccactgccag      6420
gtcctcctct taccactgtt tgctgaatgc cacaaggtcc tggctccagc cacattctat      6480
gccatctgcc agcaggacag ttgccaccag gagcaagtgt gtgaggtgat cgcctcttat      6540
gcccacctct gtcggaccaa cggggtctgc gttgactgga ggacacctga tttctgtgct      6600
atgtcatgcc caccatctct ggtttataac cactgtgagc atggctgtcc ccggcactgt      6660
gatggcaacg tgagctcctg tggggaccat ccctccgaag ctgtttctg ccctccagat       6720
aaagtcatgt tggaaggcag ctgtgtccct gaagaggcct gcactcagtg cattggtgag      6780
gatggagtcc agcaccagtt cctggaagcc tgggtcccgg accaccagcc tgtcagatc       6840
tgcacatgcc tcagcgggcg aaggtcaac tgcacaacgc agccctgccc acggccaaa        6900
gctcccacgt gtggcctgtg tgaagtagcc cgcctccgcc agaatgcaga ccagtgctgc      6960
cccgagtatg agtgtgtgtg tgacccagtg agctgtgacc tgcccccagt gcctcactgt     7020
gaacgtggcc tccagcccac actgaccaac cctggcgagt gcagacccaa cttcacctgc     7080
gcctgcagga aggaggagtg caaaagagtg tccccaccct cctgccccc gcaccgtttg       7140
cccacccttc ggaagaccca gtgctgtgat gagtatgagt gtgcctgcaa ctgtgtcaac     7200
tccacagtga gctgtcccct tgggtacttg gcctcaaccg ccaccaatga ctgtggctgt     7260
accacaacca cctgccttcc cgacaaggtg tgtgtccacc gaagcaccat ctaccctgtg    7320
ggccagttct gggaggaggg ctgcgatgtg tgcacctgca ccgacatgga ggatgccgtg    7380
atgggcctcc gcgtggccca gtgctcccag aagccctgtg aggacagctg tcggtcgggc    7440
ttcacttacg ttctgcatga aggcgagtgc tgtggaaggt gcctgccatc tgcctgtgag    7500
gtggtgactg gctcaccgcg ggggactcc cagtcttcct ggaagagtgt cggctcccag      7560
tgggcctccc cggagaaccc ctgcctcatc aatgagtgtg tccgagtgaa ggaggaggtc    7620
tttatacaac aaaggaacgt ctcctgcccc cagctggagg tccctgtctg cccctcgggc     7680
tttcagctga gctgtaagac ctcagcgtgc tgcccaagct gtcgctgtga gcgcatggag     7740
gcctgcatgc tcaatggcac tgtcattggg cccgggaaga ctgtgatgat cgatgtgtgc    7800
acgacctgcc gctgcatggt gcaggtgggg gtcatctctg gattcaagct ggagtgcagg    7860
aagaccacct gcaaccctg ccccctgggt tacaaggaag aaaataacac aggtgaatgt    7920
tgtgggagat gtttgcctac ggcttgcacc attcagctaa gaggaggaca gatcatgaca    7980
ctgaagcgtg atgagacgct ccaggatggc tgtgatactc acttctgcaa ggtcaatgag    8040
agaggagagt acttctggga gaagagggtc acaggctgcc caccctttga tgaacacaag    8100
tgtctggctg agggaggtaa aattatgaaa attccaggca cctgctgtga cacatgtgag    8160
gagcctgagt gcaacgacat cactgccagg ctgcagtatg tcaaggtggg aagctgtaag    8220
tctgaagtag aggtggatat ccactactgc cagggcaaat gtgccagcaa agccatgtac    8280
tccattgaca tcaacgatgt gcaggaccag tgctcctgct gctctccgac acggacggag    8340
cccatgcagg tggccctgca ctgcaccaat ggctctgttg tgtaccatga ggttctcaat    8400
gccatggagt gcaaatgctc ccccaggaag tgcagcaagt ga                        8442
```

<210> SEQ ID NO 2
<211> LENGTH: 2813
<212> TYPE: PRT
<213> ORGANISM: Homo sapiens

<400> SEQUENCE: 2

Met Ile Pro Ala Arg Phe Ala Gly Val Leu Leu Ala Leu Ala Leu Ile

-continued

```
1               5                   10                  15
Leu Pro Gly Thr Leu Cys Ala Glu Gly Thr Arg Gly Arg Ser Ser Thr
                20                  25                  30
Ala Arg Cys Ser Leu Phe Gly Ser Asp Phe Val Asn Thr Phe Asp Gly
                35                  40                  45
Ser Met Tyr Ser Phe Ala Gly Tyr Cys Ser Tyr Leu Leu Ala Gly Gly
                50                  55                  60
Cys Gln Lys Arg Ser Phe Ser Ile Ile Gly Asp Phe Gln Asn Gly Lys
 65             70                  75                  80
Arg Val Ser Leu Ser Val Tyr Leu Gly Glu Phe Phe Asp Ile His Leu
                85                  90                  95
Phe Val Asn Gly Thr Val Thr Gln Gly Asp Gln Arg Val Ser Met Pro
                100                 105                 110
Tyr Ala Ser Lys Gly Leu Tyr Leu Glu Thr Glu Ala Gly Tyr Tyr Lys
                115                 120                 125
Leu Ser Gly Glu Ala Tyr Gly Phe Val Ala Arg Ile Asp Gly Ser Gly
 130                 135                 140
Asn Phe Gln Val Leu Leu Ser Asp Arg Tyr Phe Asn Lys Thr Cys Gly
 145                150                 155                 160
Leu Cys Gly Asn Phe Asn Ile Phe Ala Glu Asp Asp Phe Met Thr Gln
                165                 170                 175
Glu Gly Thr Leu Thr Ser Asp Pro Tyr Asp Phe Ala Asn Ser Trp Ala
                180                 185                 190
Leu Ser Ser Gly Glu Gln Trp Cys Glu Arg Ala Ser Pro Pro Ser Ser
                195                 200                 205
Ser Cys Asn Ile Ser Ser Gly Glu Met Gln Lys Gly Leu Trp Glu Gln
 210                 215                 220
Cys Gln Leu Leu Lys Ser Thr Ser Val Phe Ala Arg Cys His Pro Leu
 225                230                 235                 240
Val Asp Pro Glu Pro Phe Val Ala Leu Cys Glu Lys Thr Leu Cys Glu
                245                 250                 255
Cys Ala Gly Gly Leu Glu Cys Ala Cys Pro Ala Leu Leu Glu Tyr Ala
                260                 265                 270
Arg Thr Cys Ala Gln Glu Gly Met Val Leu Tyr Gly Trp Thr Asp His
                275                 280                 285
Ser Ala Cys Ser Pro Val Cys Pro Ala Gly Met Glu Tyr Arg Gln Cys
 290                 295                 300
Val Ser Pro Cys Ala Arg Thr Cys Gln Ser Leu His Ile Asn Glu Met
 305                310                 315                 320
Cys Gln Glu Arg Cys Val Asp Gly Cys Ser Cys Pro Glu Gly Gln Leu
                325                 330                 335
Leu Asp Glu Gly Leu Cys Val Glu Ser Thr Glu Cys Pro Cys Val His
                340                 345                 350
Ser Gly Lys Arg Tyr Pro Pro Gly Thr Ser Leu Ser Arg Asp Cys Asn
                355                 360                 365
Thr Cys Ile Cys Arg Asn Ser Gln Trp Ile Cys Ser Asn Glu Glu Cys
                370                 375                 380
Pro Gly Glu Cys Leu Val Thr Gly Gln Ser His Phe Lys Ser Phe Asp
 385                 390                 395                 400
Asn Arg Tyr Phe Thr Phe Ser Gly Ile Cys Gln Tyr Leu Leu Ala Arg
                405                 410                 415
Asp Cys Gln Asp His Ser Phe Ser Ile Val Ile Glu Thr Val Gln Cys
                420                 425                 430
```

```
Ala Asp Asp Arg Asp Ala Val Cys Thr Arg Ser Val Thr Val Arg Leu
            435                 440                 445

Pro Gly Leu His Asn Ser Leu Val Lys Leu Lys His Gly Ala Gly Val
        450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845
```

```
Cys Val Cys Arg Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
                900                 905                 910

Gly Cys Ser His Pro Ser Val Lys Cys Lys Arg Val Thr Ile Leu
            915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn Asp Leu Thr
            995                 1000                1005

Ser Ser  Asn Leu Gln Val Glu  Glu Asp Pro Val Asp  Phe Gly Asn
1010                1015                1020

Ser Trp  Lys Val Ser Ser Gln  Cys Ala Asp Thr Arg  Lys Val Pro
1025                1030                1035

Leu Asp  Ser Ser Pro Ala Thr  Cys His Asn Asn Ile  Met Lys Gln
1040                1045                1050

Thr Met  Val Asp Ser Ser Cys  Arg Ile Leu Thr Ser  Asp Val Phe
1055                1060                1065

Gln Asp  Cys Asn Lys Leu Val  Asp Pro Glu Pro Tyr  Leu Asp Val
1070                1075                1080

Cys Ile  Tyr Asp Thr Cys Ser  Cys Glu Ser Ile Gly  Asp Cys Ala
1085                1090                1095

Cys Phe  Cys Asp Thr Ile Ala  Ala Tyr Ala His Val  Cys Ala Gln
1100                1105                1110

His Gly  Lys Val Val Thr Trp  Arg Thr Ala Thr Leu  Cys Pro Gln
1115                1120                1125

Ser Cys  Glu Glu Arg Asn Leu  Arg Glu Asn Gly Tyr  Glu Cys Glu
1130                1135                1140

Trp Arg  Tyr Asn Ser Cys Ala  Pro Ala Cys Gln Val  Thr Cys Gln
1145                1150                1155

His Pro  Glu Pro Leu Ala Cys  Pro Val Gln Cys Val  Glu Gly Cys
1160                1165                1170

His Ala  His Cys Pro Pro Gly  Lys Ile Leu Asp Glu  Leu Leu Gln
1175                1180                1185

Thr Cys  Val Asp Pro Glu Asp  Cys Pro Val Cys Glu  Val Ala Gly
1190                1195                1200

Arg Arg  Phe Ala Ser Gly Lys  Lys Val Thr Leu Asn  Pro Ser Asp
1205                1210                1215

Pro Glu  His Cys Gln Ile Cys  His Cys Asp Val Val  Asn Leu Thr
1220                1225                1230

Cys Glu  Ala Cys Gln Glu Pro  Gly Gly Leu Val Val  Pro Pro Thr
1235                1240                1245

Asp Ala  Pro Val Ser Pro Thr  Thr Leu Tyr Val Glu  Asp Ile Ser
```

```
            1250                1255                1260
Glu Pro Pro Leu His Asp Phe Tyr Cys Ser Arg Leu Leu Asp Leu
        1265                1270                1275
Val Phe Leu Leu Asp Gly Ser Ser Arg Leu Ser Glu Ala Glu Phe
        1280                1285                1290
Glu Val Leu Lys Ala Phe Val Val Asp Met Met Glu Arg Leu Arg
        1295                1300                1305
Ile Ser Gln Lys Trp Val Val Ala Val Val Glu Tyr His Asp
        1310                1315                1320
Gly Ser His Ala Tyr Ile Gly Leu Lys Asp Arg Lys Arg Pro Ser
        1325                1330                1335
Glu Leu Arg Arg Ile Ala Ser Gln Val Lys Tyr Ala Gly Ser Gln
        1340                1345                1350
Val Ala Ser Thr Ser Glu Val Leu Lys Tyr Thr Leu Phe Gln Ile
        1355                1360                1365
Phe Ser Lys Ile Asp Arg Pro Glu Ala Ser Arg Ile Thr Leu Leu
        1370                1375                1380
Leu Met Ala Ser Gln Glu Pro Gln Arg Met Ser Arg Asn Phe Val
        1385                1390                1395
Arg Tyr Val Gln Gly Leu Lys Lys Lys Val Ile Val Ile Pro
        1400                1405                1410
Val Gly Ile Gly Pro His Ala Asn Leu Lys Gln Ile Arg Leu Ile
        1415                1420                1425
Glu Lys Gln Ala Pro Glu Asn Lys Ala Phe Val Leu Ser Ser Val
        1430                1435                1440
Asp Glu Leu Glu Gln Gln Arg Asp Glu Ile Val Ser Tyr Leu Cys
        1445                1450                1455
Asp Leu Ala Pro Glu Ala Pro Pro Pro Thr Leu Pro Pro Asp Met
        1460                1465                1470
Ala Gln Val Thr Val Gly Pro Gly Leu Leu Gly Val Ser Thr Leu
        1475                1480                1485
Gly Pro Lys Arg Asn Ser Met Val Leu Asp Val Ala Phe Val Leu
        1490                1495                1500
Glu Gly Ser Asp Lys Ile Gly Glu Ala Asp Phe Asn Arg Ser Lys
        1505                1510                1515
Glu Phe Met Glu Glu Val Ile Gln Arg Met Asp Val Gly Gln Asp
        1520                1525                1530
Ser Ile His Val Thr Val Leu Gln Tyr Ser Tyr Met Val Thr Val
        1535                1540                1545
Glu Tyr Pro Phe Ser Glu Ala Gln Ser Lys Gly Asp Ile Leu Gln
        1550                1555                1560
Arg Val Arg Glu Ile Arg Tyr Gln Gly Gly Asn Arg Thr Asn Thr
        1565                1570                1575
Gly Leu Ala Leu Arg Tyr Leu Ser Asp His Ser Phe Leu Val Ser
        1580                1585                1590
Gln Gly Asp Arg Glu Gln Ala Pro Asn Leu Val Tyr Met Val Thr
        1595                1600                1605
Gly Asn Pro Ala Ser Asp Glu Ile Lys Arg Leu Pro Gly Asp Ile
        1610                1615                1620
Gln Val Val Pro Ile Gly Val Gly Pro Asn Ala Asn Val Gln Glu
        1625                1630                1635
Leu Glu Arg Ile Gly Trp Pro Asn Ala Pro Ile Leu Ile Gln Asp
        1640                1645                1650
```

-continued

```
Phe Glu Thr Leu Pro Arg Glu Ala Pro Asp Leu Val Leu Gln Arg
    1655             1660             1665

Cys Cys Ser Gly Glu Gly Leu Gln Ile Pro Thr Leu Ser Pro Ala
    1670             1675             1680

Pro Asp Cys Ser Gln Pro Leu Asp Val Ile Leu Leu Leu Asp Gly
    1685             1690             1695

Ser Ser Ser Phe Pro Ala Ser Tyr Phe Asp Glu Met Lys Ser Phe
    1700             1705             1710

Ala Lys Ala Phe Ile Ser Lys Ala Asn Ile Gly Pro Arg Leu Thr
    1715             1720             1725

Gln Val Ser Val Leu Gln Tyr Gly Ser Ile Thr Thr Ile Asp Val
    1730             1735             1740

Pro Trp Asn Val Val Pro Glu Lys Ala His Leu Leu Ser Leu Val
    1745             1750             1755

Asp Val Met Gln Arg Glu Gly Gly Pro Ser Gln Ile Gly Asp Ala
    1760             1765             1770

Leu Gly Phe Ala Val Arg Tyr Leu Thr Ser Glu Met His Gly Ala
    1775             1780             1785

Arg Pro Gly Ala Ser Lys Ala Val Val Ile Leu Val Thr Asp Val
    1790             1795             1800

Ser Val Asp Ser Val Asp Ala Ala Ala Asp Ala Ala Arg Ser Asn
    1805             1810             1815

Arg Val Thr Val Phe Pro Ile Gly Ile Gly Asp Arg Tyr Asp Ala
    1820             1825             1830

Ala Gln Leu Arg Ile Leu Ala Gly Pro Ala Gly Asp Ser Asn Val
    1835             1840             1845

Val Lys Leu Gln Arg Ile Glu Asp Leu Pro Thr Met Val Thr Leu
    1850             1855             1860

Gly Asn Ser Phe Leu His Lys Leu Cys Ser Gly Phe Val Arg Ile
    1865             1870             1875

Cys Met Asp Glu Asp Gly Asn Glu Lys Arg Pro Gly Asp Val Trp
    1880             1885             1890

Thr Leu Pro Asp Gln Cys His Thr Val Thr Cys Gln Pro Asp Gly
    1895             1900             1905

Gln Thr Leu Leu Lys Ser His Arg Val Asn Cys Asp Arg Gly Leu
    1910             1915             1920

Arg Pro Ser Cys Pro Asn Ser Gln Ser Pro Val Lys Val Glu Glu
    1925             1930             1935

Thr Cys Gly Cys Arg Trp Thr Cys Pro Cys Val Cys Thr Gly Ser
    1940             1945             1950

Ser Thr Arg His Ile Val Thr Phe Asp Gly Gln Asn Phe Lys Leu
    1955             1960             1965

Thr Gly Ser Cys Ser Tyr Val Leu Phe Gln Asn Lys Glu Gln Asp
    1970             1975             1980

Leu Glu Val Ile Leu His Asn Gly Ala Cys Ser Pro Gly Ala Arg
    1985             1990             1995

Gln Gly Cys Met Lys Ser Ile Glu Val Lys His Ser Ala Leu Ser
    2000             2005             2010

Val Glu Leu His Ser Asp Met Glu Val Thr Val Asn Gly Arg Leu
    2015             2020             2025

Val Ser Val Pro Tyr Val Gly Gly Asn Met Glu Val Asn Val Tyr
    2030             2035             2040
```

-continued

```
Gly Ala Ile Met His Glu Val Arg Phe Asn His Leu Gly His Ile
    2045                2050                2055
Phe Thr Phe Thr Pro Gln Asn Asn Glu Phe Gln Leu Gln Leu Ser
    2060                2065                2070
Pro Lys Thr Phe Ala Ser Lys Thr Tyr Gly Leu Cys Gly Ile Cys
    2075                2080                2085
Asp Glu Asn Gly Ala Asn Asp Phe Met Leu Arg Asp Gly Thr Val
    2090                2095                2100
Thr Thr Asp Trp Lys Thr Leu Val Gln Glu Trp Thr Val Gln Arg
    2105                2110                2115
Pro Gly Gln Thr Cys Gln Pro Ile Leu Glu Glu Gln Cys Leu Val
    2120                2125                2130
Pro Asp Ser Ser His Cys Gln Val Leu Leu Leu Pro Leu Phe Ala
    2135                2140                2145
Glu Cys His Lys Val Leu Ala Pro Ala Thr Phe Tyr Ala Ile Cys
    2150                2155                2160
Gln Gln Asp Ser Cys His Gln Glu Gln Val Cys Glu Val Ile Ala
    2165                2170                2175
Ser Tyr Ala His Leu Cys Arg Thr Asn Gly Val Cys Val Asp Trp
    2180                2185                2190
Arg Thr Pro Asp Phe Cys Ala Met Ser Cys Pro Pro Ser Leu Val
    2195                2200                2205
Tyr Asn His Cys Glu His Gly Cys Pro Arg His Cys Asp Gly Asn
    2210                2215                2220
Val Ser Ser Cys Gly Asp His Pro Ser Glu Gly Cys Phe Cys Pro
    2225                2230                2235
Pro Asp Lys Val Met Leu Glu Gly Ser Cys Val Pro Glu Glu Ala
    2240                2245                2250
Cys Thr Gln Cys Ile Gly Glu Asp Gly Val Gln His Gln Phe Leu
    2255                2260                2265
Glu Ala Trp Val Pro Asp His Gln Pro Cys Gln Ile Cys Thr Cys
    2270                2275                2280
Leu Ser Gly Arg Lys Val Asn Cys Thr Thr Gln Pro Cys Pro Thr
    2285                2290                2295
Ala Lys Ala Pro Thr Cys Gly Leu Cys Glu Val Ala Arg Leu Arg
    2300                2305                2310
Gln Asn Ala Asp Gln Cys Cys Pro Glu Tyr Glu Cys Val Cys Asp
    2315                2320                2325
Pro Val Ser Cys Asp Leu Pro Pro Val Pro His Cys Glu Arg Gly
    2330                2335                2340
Leu Gln Pro Thr Leu Thr Asn Pro Gly Glu Cys Arg Pro Asn Phe
    2345                2350                2355
Thr Cys Ala Cys Arg Lys Glu Glu Cys Lys Arg Val Ser Pro Pro
    2360                2365                2370
Ser Cys Pro Pro His Arg Leu Pro Thr Leu Arg Lys Thr Gln Cys
    2375                2380                2385
Cys Asp Glu Tyr Glu Cys Ala Cys Asn Cys Val Asn Ser Thr Val
    2390                2395                2400
Ser Cys Pro Leu Gly Tyr Leu Ala Ser Thr Ala Thr Asn Asp Cys
    2405                2410                2415
Gly Cys Thr Thr Thr Thr Cys Leu Pro Asp Lys Val Cys Val His
    2420                2425                2430
Arg Ser Thr Ile Tyr Pro Val Gly Gln Phe Trp Glu Glu Gly Cys
```

-continued

```
              2435                2440                2445

Asp Val Cys Thr Cys Thr Asp Met Glu Asp Ala Val Met Gly Leu
    2450                2455                2460

Arg Val Ala Gln Cys Ser Gln Lys Pro Cys Glu Asp Ser Cys Arg
    2465                2470                2475

Ser Gly Phe Thr Tyr Val Leu His Glu Gly Glu Cys Cys Gly Arg
    2480                2485                2490

Cys Leu Pro Ser Ala Cys Glu Val Val Thr Gly Ser Pro Arg Gly
    2495                2500                2505

Asp Ser Gln Ser Ser Trp Lys Ser Val Gly Ser Gln Trp Ala Ser
    2510                2515                2520

Pro Glu Asn Pro Cys Leu Ile Asn Glu Cys Val Arg Val Lys Glu
    2525                2530                2535

Glu Val Phe Ile Gln Gln Arg Asn Val Ser Cys Pro Gln Leu Glu
    2540                2545                2550

Val Pro Val Cys Pro Ser Gly Phe Gln Leu Ser Cys Lys Thr Ser
    2555                2560                2565

Ala Cys Cys Pro Ser Cys Arg Cys Glu Arg Met Glu Ala Cys Met
    2570                2575                2580

Leu Asn Gly Thr Val Ile Gly Pro Gly Lys Thr Val Met Ile Asp
    2585                2590                2595

Val Cys Thr Thr Cys Arg Cys Met Val Gln Val Gly Val Ile Ser
    2600                2605                2610

Gly Phe Lys Leu Glu Cys Arg Lys Thr Thr Cys Asn Pro Cys Pro
    2615                2620                2625

Leu Gly Tyr Lys Glu Glu Asn Thr Gly Glu Cys Cys Gly Arg
    2630                2635                2640

Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810

<210> SEQ ID NO 3
```

```
<211> LENGTH: 30
<212> TYPE: DNA
<213> ORGANISM: Artificial Sequence
<220> FEATURE:
<223> OTHER INFORMATION: Primer VWF+

<400> SEQUENCE: 3
ttcgaattcc cgcagccctc atttgcaggg                                        30

<210> SEQ ID NO 4
<211> LENGTH: 31
<212> TYPE: DNA
<213> ORGANISM: Artificial Sequence
<220> FEATURE:
<223> OTHER INFORMATION: Primer VWF-

<400> SEQUENCE: 4
tccgaattcc ggcagcagca ggcacccatg c                                      31

<210> SEQ ID NO 5
<211> LENGTH: 29
<212> TYPE: DNA
<213> ORGANISM: Artificial Sequence
<220> FEATURE:
<223> OTHER INFORMATION: Primer We4070

<400> SEQUENCE: 5
ggtgtgtccc gctaacaacc tgcgggctg                                         29

<210> SEQ ID NO 6
<211> LENGTH: 29
<212> TYPE: DNA
<213> ORGANISM: Artificial Sequence
<220> FEATURE:
<223> OTHER INFORMATION: Primer We4071

<400> SEQUENCE: 6
cagcccgcag gttgttagcg ggacacacc                                         29

<210> SEQ ID NO 7
<211> LENGTH: 29
<212> TYPE: DNA
<213> ORGANISM: Artificial Sequence
<220> FEATURE:
<223> OTHER INFORMATION: Pirmer We4072

<400> SEQUENCE: 7
gtcccgctga caaccctcgg gctgaaggg                                         29

<210> SEQ ID NO 8
<211> LENGTH: 29
<212> TYPE: DNA
<213> ORGANISM: Artificial Sequence
<220> FEATURE:
<223> OTHER INFORMATION: Primer We4073

<400> SEQUENCE: 8
cccttcagcc cgagggttgt cagcgggac                                         29

<210> SEQ ID NO 9
<211> LENGTH: 35
<212> TYPE: DNA
<213> ORGANISM: Artificial Sequence
<220> FEATURE:
<223> OTHER INFORMATION: Primer We4074

<400> SEQUENCE: 9
```
ctgaagggct cgagtgtgcc aaaacgtgcc agaac                                35

<210> SEQ ID NO 10
<211> LENGTH: 35
<212> TYPE: DNA
<213> ORGANISM: Artificial Sequence
<220> FEATURE:
<223> OTHER INFORMATION: Primer We4075

<400> SEQUENCE: 10
gttctggcac gttttggcac actcgagccc ttcag                                35

<210> SEQ ID NO 11
<211> LENGTH: 37
<212> TYPE: DNA
<213> ORGANISM: Artificial Sequence
<220> FEATURE:
<223> OTHER INFORMATION: Primer We4076

<400> SEQUENCE: 11
gtgtaccaaa acgtgccgga actatgacct ggagtgc                              37

<210> SEQ ID NO 12
<211> LENGTH: 37
<212> TYPE: DNA
<213> ORGANISM: Artificial Sequence
<220> FEATURE:
<223> OTHER INFORMATION: Primer We4077

<400> SEQUENCE: 12
gcactccagg tcatagttcc ggcacgtttt ggtacac                              37

<210> SEQ ID NO 13
<211> LENGTH: 35
<212> TYPE: DNA
<213> ORGANISM: Artificial Sequence
<220> FEATURE:
<223> OTHER INFORMATION: Primer We4078

<400> SEQUENCE: 13
gtaccaaaac gtgccagaag tatgacctgg agtgc                                35

<210> SEQ ID NO 14
<211> LENGTH: 35
<212> TYPE: DNA
<213> ORGANISM: Artificial Sequence
<220> FEATURE:
<223> OTHER INFORMATION: We4079

<400> SEQUENCE: 14
gcactccagg tcatacttct ggcacgtttt ggtac                                35

<210> SEQ ID NO 15
<211> LENGTH: 35
<212> TYPE: DNA
<213> ORGANISM: Artificial Sequence
<220> FEATURE:
<223> OTHER INFORMATION: Primer We4080

<400> SEQUENCE: 15
ctggagtgca tgagcagggg ctgtgtctct ggctg                                35

<210> SEQ ID NO 16
<211> LENGTH: 35
<212> TYPE: DNA

<213> ORGANISM: Artificial Sequence
<220> FEATURE:
<223> OTHER INFORMATION: Primer We4081

<400> SEQUENCE: 16
cagccagaga cacagcccct gctcatgcac tccag          35

<210> SEQ ID NO 17
<211> LENGTH: 35
<212> TYPE: DNA
<213> ORGANISM: Artificial Sequence
<220> FEATURE:
<223> OTHER INFORMATION: Primer We4082

<400> SEQUENCE: 17
ctggagtgca tgagcaaggg ctgtgtctct ggctg          35

<210> SEQ ID NO 18
<211> LENGTH: 35
<212> TYPE: DNA
<213> ORGANISM: Artificial Sequence
<220> FEATURE:
<223> OTHER INFORMATION: Primer We4083

<400> SEQUENCE: 18
cagccagaga cacagcccTt gctcatgcac tccag          35

<210> SEQ ID NO 19
<211> LENGTH: 34
<212> TYPE: DNA
<213> ORGANISM: Artificial Sequence
<220> FEATURE:
<223> OTHER INFORMATION: Primer We4084

<400> SEQUENCE: 19
catggtccgg catgccaaca gatgtgtggc cctg          34

<210> SEQ ID NO 20
<211> LENGTH: 34
<212> TYPE: DNA
<213> ORGANISM: Artificial Sequence
<220> FEATURE:
<223> OTHER INFORMATION: Primer We4085

<400> SEQUENCE: 20
cagggccaca catctgttgg catgccggac catg          34

<210> SEQ ID NO 21
<211> LENGTH: 34
<212> TYPE: DNA
<213> ORGANISM: Artificial Sequence
<220> FEATURE:
<223> OTHER INFORMATION: Primer We4086

<400> SEQUENCE: 21
catggtccgg cataagaaca gatgtgtggc cctg          34

<210> SEQ ID NO 22
<211> LENGTH: 34
<212> TYPE: DNA
<213> ORGANISM: Artificial Sequence
<220> FEATURE:
<223> OTHER INFORMATION: Primer We4087

<400> SEQUENCE: 22
cagggccaca catctgttct tatgccggac catg          34

<210> SEQ ID NO 23
<211> LENGTH: 31
<212> TYPE: DNA
<213> ORGANISM: Artificial Sequence
<220> FEATURE:
<223> OTHER INFORMATION: Primer We4088

<400> SEQUENCE: 23
ggtccggcat gagaagagat gtgtggccct g        31

<210> SEQ ID NO 24
<211> LENGTH: 31
<212> TYPE: DNA
<213> ORGANISM: Artificial Sequence
<220> FEATURE:
<223> OTHER INFORMATION: Primer We4089

<400> SEQUENCE: 24
cagggccaca catctcttct catgccggac c        31

<210> SEQ ID NO 25
<211> LENGTH: 37
<212> TYPE: DNA
<213> ORGANISM: Artificial Sequence
<220> FEATURE:
<223> OTHER INFORMATION: Primer We4090

<400> SEQUENCE: 25
gcttccatca gggcaagcag tatgcccctg gagaaac        37

<210> SEQ ID NO 26
<211> LENGTH: 37
<212> TYPE: DNA
<213> ORGANISM: Artificial Sequence
<220> FEATURE:
<223> OTHER INFORMATION: Primer We4091

<400> SEQUENCE: 26
gtttctccag gggcatactg cttgccctga tggaagc        37

<210> SEQ ID NO 27
<211> LENGTH: 39
<212> TYPE: DNA
<213> ORGANISM: Artificial Sequence
<220> FEATURE:
<223> OTHER INFORMATION: Primer We4092

<400> SEQUENCE: 27
gggcaaggag tatgccaagg gagaaacagt gaagattgg        39

<210> SEQ ID NO 28
<211> LENGTH: 39
<212> TYPE: DNA
<213> ORGANISM: Artificial Sequence
<220> FEATURE:
<223> OTHER INFORMATION: Primer We4093

<400> SEQUENCE: 28
ccaatcttca ctgtttctcc cttggcatac tccttgccc        39

<210> SEQ ID NO 29
<211> LENGTH: 35
<212> TYPE: DNA
<213> ORGANISM: Artificial Sequence
<220> FEATURE:

<223> OTHER INFORMATION: Primer We4094

<400> SEQUENCE: 29
cggaaccgga agtggaactg cacagaccat gtgtg                                    35

<210> SEQ ID NO 30
<211> LENGTH: 35
<212> TYPE: DNA
<213> ORGANISM: Artificial Sequence
<220> FEATURE:
<223> OTHER INFORMATION: Primer We4095

<400> SEQUENCE: 30
cacacatggt ctgtgcagtt ccacttccgg ttccg                                    35

<210> SEQ ID NO 31
<211> LENGTH: 102
<212> TYPE: PRT
<213> ORGANISM: Homo sapiens

<400> SEQUENCE: 31

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
                20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
        50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala
            100

<210> SEQ ID NO 32
<211> LENGTH: 2050
<212> TYPE: PRT
<213> ORGANISM: Homo sapiens

<400> SEQUENCE: 32

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
                20                  25                  30

Asp Leu Glu Cys Met Ser Met Gly Cys Val Ser Gly Cys Leu Cys Pro
            35                  40                  45

Pro Gly Met Val Arg His Glu Asn Arg Cys Val Ala Leu Glu Arg Cys
        50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

-continued

```
Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Leu
465                 470                 475                 480

Val Val Pro Pro Thr Asp Ala Pro Val Ser Pro Thr Thr Leu Tyr Val
                485                 490                 495

Glu Asp Ile Ser Glu Pro Pro Leu His Asp Phe Tyr Cys Ser Arg Leu
            500                 505                 510

Leu Asp Leu Val Phe Leu Leu Asp Gly Ser Ser Arg Leu Ser Glu Ala
        515                 520                 525

Glu Phe Glu Val Leu Lys Ala Phe Val Val Asp Met Met Glu Arg Leu
    530                 535                 540

Arg Ile Ser Gln Lys Trp Val Arg Val Ala Val Val Glu Tyr His Asp
```

-continued

```
        545                 550                 555                 560
    Gly Ser His Ala Tyr Ile Gly Leu Lys Asp Arg Lys Pro Ser Glu
                    565                 570                 575

Leu Arg Arg Ile Ala Ser Gln Val Lys Tyr Ala Gly Ser Gln Val Ala
                    580                 585                 590

Ser Thr Ser Glu Val Leu Lys Tyr Thr Leu Phe Gln Ile Phe Ser Lys
                    595                 600                 605

Ile Asp Arg Pro Glu Ala Ser Arg Ile Thr Leu Leu Leu Met Ala Ser
                    610                 615                 620

Gln Glu Pro Gln Arg Met Ser Arg Asn Phe Val Arg Tyr Val Gln Gly
    625                 630                 635                 640

Leu Lys Lys Lys Val Ile Val Ile Pro Val Gly Ile Gly Pro His
                    645                 650                 655

Ala Asn Leu Lys Gln Ile Arg Leu Ile Glu Lys Gln Ala Pro Glu Asn
                    660                 665                 670

Lys Ala Phe Val Leu Ser Ser Val Asp Glu Leu Glu Gln Gln Arg Asp
                    675                 680                 685

Glu Ile Val Ser Tyr Leu Cys Asp Leu Ala Pro Glu Ala Pro Pro
        690                 695                 700

Thr Leu Pro Pro Asp Met Ala Gln Val Thr Val Gly Pro Gly Leu Leu
    705                 710                 715                 720

Gly Val Ser Thr Leu Gly Pro Lys Arg Asn Ser Met Val Leu Asp Val
                    725                 730                 735

Ala Phe Val Leu Glu Gly Ser Asp Lys Ile Gly Glu Ala Asp Phe Asn
                    740                 745                 750

Arg Ser Lys Glu Phe Met Glu Glu Val Ile Gln Arg Met Asp Val Gly
                    755                 760                 765

Gln Asp Ser Ile His Val Thr Val Leu Gln Tyr Ser Tyr Met Val Thr
                    770                 775                 780

Val Glu Tyr Pro Phe Ser Glu Ala Gln Ser Lys Gly Asp Ile Leu Gln
    785                 790                 795                 800

Arg Val Arg Glu Ile Arg Tyr Gln Gly Gly Asn Arg Thr Asn Thr Gly
                    805                 810                 815

Leu Ala Leu Arg Tyr Leu Ser Asp His Ser Phe Leu Val Ser Gln Gly
                    820                 825                 830

Asp Arg Glu Gln Ala Pro Asn Leu Val Tyr Met Val Thr Gly Asn Pro
                    835                 840                 845

Ala Ser Asp Glu Ile Lys Arg Leu Pro Gly Asp Ile Gln Val Val Pro
                    850                 855                 860

Ile Gly Val Gly Pro Asn Ala Asn Val Gln Glu Leu Glu Arg Ile Gly
    865                 870                 875                 880

Trp Pro Asn Ala Pro Ile Leu Ile Gln Asp Phe Glu Thr Leu Pro Arg
                    885                 890                 895

Glu Ala Pro Asp Leu Val Leu Gln Arg Cys Cys Ser Gly Glu Gly Leu
                    900                 905                 910

Gln Ile Pro Thr Leu Ser Pro Ala Pro Asp Cys Ser Gln Pro Leu Asp
                    915                 920                 925

Val Ile Leu Leu Leu Asp Gly Ser Ser Ser Phe Pro Ala Ser Tyr Phe
                    930                 935                 940

Asp Glu Met Lys Ser Phe Ala Lys Ala Phe Ile Ser Lys Ala Asn Ile
    945                 950                 955                 960

Gly Pro Arg Leu Thr Gln Val Ser Val Leu Gln Tyr Gly Ser Ile Thr
                    965                 970                 975
```

-continued

```
Thr Ile Asp Val Pro Trp Asn Val Pro Glu Lys Ala His Leu Leu
            980                 985                 990

Ser Leu Val Asp Val Met Gln Arg Glu Gly Gly Pro Ser Gln Ile Gly
            995                 1000                1005

Asp Ala Leu Gly Phe Ala Val Arg Tyr Leu Thr Ser Glu Met His
        1010                1015                1020

Gly Ala Arg Pro Gly Ala Ser Lys Ala Val Val Ile Leu Val Thr
        1025                1030                1035

Asp Val Ser Val Asp Ser Val Asp Ala Ala Asp Ala Ala Arg
        1040                1045                1050

Ser Asn Arg Val Thr Val Phe Pro Ile Gly Ile Gly Asp Arg Tyr
        1055                1060                1065

Asp Ala Ala Gln Leu Arg Ile Leu Ala Gly Pro Ala Gly Asp Ser
        1070                1075                1080

Asn Val Val Lys Leu Gln Arg Ile Glu Asp Leu Pro Thr Met Val
        1085                1090                1095

Thr Leu Gly Asn Ser Phe Leu His Lys Leu Cys Ser Gly Phe Val
        1100                1105                1110

Arg Ile Cys Met Asp Glu Asp Gly Asn Glu Lys Arg Pro Gly Asp
        1115                1120                1125

Val Trp Thr Leu Pro Asp Gln Cys His Thr Val Thr Cys Gln Pro
        1130                1135                1140

Asp Gly Gln Thr Leu Leu Lys Ser His Arg Val Asn Cys Asp Arg
        1145                1150                1155

Gly Leu Arg Pro Ser Cys Pro Asn Ser Gln Ser Pro Val Lys Val
        1160                1165                1170

Glu Glu Thr Cys Gly Cys Arg Trp Thr Cys Pro Cys Val Cys Thr
        1175                1180                1185

Gly Ser Ser Thr Arg His Ile Val Thr Phe Asp Gly Gln Asn Phe
        1190                1195                1200

Lys Leu Thr Gly Ser Cys Ser Tyr Val Leu Phe Gln Asn Lys Glu
        1205                1210                1215

Gln Asp Leu Glu Val Ile Leu His Asn Gly Ala Cys Ser Pro Gly
        1220                1225                1230

Ala Arg Gln Gly Cys Met Lys Ser Ile Glu Val Lys His Ser Ala
        1235                1240                1245

Leu Ser Val Glu Leu His Ser Asp Met Glu Val Thr Val Asn Gly
        1250                1255                1260

Arg Leu Val Ser Val Pro Tyr Val Gly Gly Asn Met Glu Val Asn
        1265                1270                1275

Val Tyr Gly Ala Ile Met His Glu Val Arg Phe Asn His Leu Gly
        1280                1285                1290

His Ile Phe Thr Phe Thr Pro Gln Asn Asn Glu Phe Gln Leu Gln
        1295                1300                1305

Leu Ser Pro Lys Thr Phe Ala Ser Lys Thr Tyr Gly Leu Cys Gly
        1310                1315                1320

Ile Cys Asp Glu Asn Gly Ala Asn Asp Phe Met Leu Arg Asp Gly
        1325                1330                1335

Thr Val Thr Thr Asp Trp Lys Thr Leu Val Gln Glu Trp Thr Val
        1340                1345                1350

Gln Arg Pro Gly Gln Thr Cys Gln Pro Ile Leu Glu Glu Gln Cys
        1355                1360                1365
```

```
Leu Val Pro Asp Ser Ser His Cys Gln Val Leu Leu Leu Pro Leu
    1370            1375                1380

Phe Ala Glu Cys His Lys Val Leu Ala Pro Ala Thr Phe Tyr Ala
    1385            1390                1395

Ile Cys Gln Gln Asp Ser Cys His Gln Glu Gln Val Cys Glu Val
    1400            1405                1410

Ile Ala Ser Tyr Ala His Leu Cys Arg Thr Asn Gly Val Cys Val
    1415            1420                1425

Asp Trp Arg Thr Pro Asp Phe Cys Ala Met Ser Cys Pro Pro Ser
    1430            1435                1440

Leu Val Tyr Asn His Cys Glu His Gly Cys Pro Arg His Cys Asp
    1445            1450                1455

Gly Asn Val Ser Ser Cys Gly Asp His Pro Ser Glu Gly Cys Phe
    1460            1465                1470

Cys Pro Pro Asp Lys Val Met Leu Glu Gly Ser Cys Val Pro Glu
    1475            1480                1485

Glu Ala Cys Thr Gln Cys Ile Gly Glu Asp Gly Val Gln His Gln
    1490            1495                1500

Phe Leu Glu Ala Trp Val Pro Asp His Gln Pro Cys Gln Ile Cys
    1505            1510                1515

Thr Cys Leu Ser Gly Arg Lys Val Asn Cys Thr Thr Gln Pro Cys
    1520            1525                1530

Pro Thr Ala Lys Ala Pro Thr Cys Gly Leu Cys Glu Val Ala Arg
    1535            1540                1545

Leu Arg Gln Asn Ala Asp Gln Cys Cys Pro Glu Tyr Glu Cys Val
    1550            1555                1560

Cys Asp Pro Val Ser Cys Asp Leu Pro Pro Val Pro His Cys Glu
    1565            1570                1575

Arg Gly Leu Gln Pro Thr Leu Thr Asn Pro Gly Glu Cys Arg Pro
    1580            1585                1590

Asn Phe Thr Cys Ala Cys Arg Lys Glu Glu Cys Lys Arg Val Ser
    1595            1600                1605

Pro Pro Ser Cys Pro Pro His Arg Leu Pro Thr Leu Arg Lys Thr
    1610            1615                1620

Gln Cys Cys Asp Glu Tyr Glu Cys Ala Cys Asn Cys Val Asn Ser
    1625            1630                1635

Thr Val Ser Cys Pro Leu Gly Tyr Leu Ala Ser Thr Ala Thr Asn
    1640            1645                1650

Asp Cys Gly Cys Thr Thr Thr Thr Cys Leu Pro Asp Lys Val Cys
    1655            1660                1665

Val His Arg Ser Thr Ile Tyr Pro Val Gly Gln Phe Trp Glu Glu
    1670            1675                1680

Gly Cys Asp Val Cys Thr Cys Thr Asp Met Glu Asp Ala Val Met
    1685            1690                1695

Gly Leu Arg Val Ala Gln Cys Ser Gln Lys Pro Cys Glu Asp Ser
    1700            1705                1710

Cys Arg Ser Gly Phe Thr Tyr Val Leu His Glu Gly Glu Cys Cys
    1715            1720                1725

Gly Arg Cys Leu Pro Ser Ala Cys Glu Val Val Thr Gly Ser Pro
    1730            1735                1740

Arg Gly Asp Ser Gln Ser Ser Trp Lys Ser Val Gly Ser Gln Trp
    1745            1750                1755

Ala Ser Pro Glu Asn Pro Cys Leu Ile Asn Glu Cys Val Arg Val
```

```
                    1760                1765                1770
Lys Glu Glu Val Phe Ile Gln Gln Arg Asn Val Ser Cys Pro Gln
    1775                1780                1785

Leu Glu Val Pro Val Cys Pro Ser Gly Phe Gln Leu Ser Cys Lys
    1790                1795                1800

Thr Ser Ala Cys Cys Pro Ser Cys Arg Cys Glu Arg Met Glu Ala
    1805                1810                1815

Cys Met Leu Asn Gly Thr Val Ile Gly Pro Gly Lys Thr Val Met
    1820                1825                1830

Ile Asp Val Cys Thr Thr Cys Arg Cys Met Val Gln Val Gly Val
    1835                1840                1845

Ile Ser Gly Phe Lys Leu Glu Cys Arg Lys Thr Thr Cys Asn Pro
    1850                1855                1860

Cys Pro Leu Gly Tyr Lys Glu Glu Asn Asn Thr Gly Glu Cys Cys
    1865                1870                1875

Gly Arg Cys Leu Pro Thr Ala Cys Thr Ile Gln Leu Arg Gly Gly
    1880                1885                1890

Gln Ile Met Thr Leu Lys Arg Asp Glu Thr Leu Gln Asp Gly Cys
    1895                1900                1905

Asp Thr His Phe Cys Lys Val Asn Glu Arg Gly Glu Tyr Phe Trp
    1910                1915                1920

Glu Lys Arg Val Thr Gly Cys Pro Pro Phe Asp Glu His Lys Cys
    1925                1930                1935

Leu Ala Glu Gly Gly Lys Ile Met Lys Ile Pro Gly Thr Cys Cys
    1940                1945                1950

Asp Thr Cys Glu Glu Pro Glu Cys Asn Asp Ile Thr Ala Arg Leu
    1955                1960                1965

Gln Tyr Val Lys Val Gly Ser Cys Lys Ser Glu Val Glu Val Asp
    1970                1975                1980

Ile His Tyr Cys Gln Gly Lys Cys Ala Ser Lys Ala Met Tyr Ser
    1985                1990                1995

Ile Asp Ile Asn Asp Val Gln Asp Gln Cys Ser Cys Cys Ser Pro
    2000                2005                2010

Thr Arg Thr Glu Pro Met Gln Val Ala Leu His Cys Thr Asn Gly
    2015                2020                2025

Ser Val Val Tyr His Glu Val Leu Asn Ala Met Glu Cys Lys Cys
    2030                2035                2040

Ser Pro Arg Lys Cys Ser Lys
    2045                2050

<210> SEQ ID NO 33
<211> LENGTH: 102
<212> TYPE: PRT
<213> ORGANISM: Artificial sequence
<220> FEATURE:
<223> OTHER INFORMATION: Modified D' domain of VWF
<220> FEATURE:
<221> NAME/KEY: MISC_FEATURE
<222> LOCATION: (16)..(16)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is Leu or Pro
<220> FEATURE:
<221> NAME/KEY: MISC_FEATURE
<222> LOCATION: (24)..(24)
<223> OTHER INFORMATION: Xaa is any amino acid
<220> FEATURE:
```

```
<221> NAME/KEY: MISC_FEATURE
<222> LOCATION: (26)..(26)
<223> OTHER INFORMATION: Xaa is any amino acid
<220> FEATURE:
<221> NAME/KEY: MISC_FEATURE
<222> LOCATION: (30)..(30)
<223> OTHER INFORMATION: Xaa is any amino acid
<220> FEATURE:
<221> NAME/KEY: MISC_FEATURE
<222> LOCATION: (31)..(31)
<223> OTHER INFORMATION: Xaa is any amino acid
<220> FEATURE:
<221> NAME/KEY: MISC_FEATURE
<222> LOCATION: (33)..(33)
<223> OTHER INFORMATION: Xaa is any amino acid
<220> FEATURE:
<221> NAME/KEY: MISC_FEATURE
<222> LOCATION: (35)..(35)
<223> OTHER INFORMATION: Xaa is any amino acid
<220> FEATURE:
<221> NAME/KEY: MISC_FEATURE
<222> LOCATION: (39)..(39)
<223> OTHER INFORMATION: Xaa is any amino acid
<220> FEATURE:
<221> NAME/KEY: MISC_FEATURE
<222> LOCATION: (55)..(55)
<223> OTHER INFORMATION: Xaa is any amino acid
<220> FEATURE:
<221> NAME/KEY: MISC_FEATURE
<222> LOCATION: (56)..(56)
<223> OTHER INFORMATION: Xaa is any amino acid
<220> FEATURE:
<221> NAME/KEY: MISC_FEATURE
<222> LOCATION: (62)..(62)
<223> OTHER INFORMATION: Xaa is any amino acid
<220> FEATURE:
<221> NAME/KEY: MISC_FEATURE
<222> LOCATION: (72)..(72)
<223> OTHER INFORMATION: Xaa is any amino acid
<220> FEATURE:
<221> NAME/KEY: MISC_FEATURE
<222> LOCATION: (75)..(75)
<223> OTHER INFORMATION: Xaa is any amino acid
<220> FEATURE:
<221> NAME/KEY: MISC_FEATURE
<222> LOCATION: (90)..(90)
<223> OTHER INFORMATION: Xaa is any amino acid

<400> SEQUENCE: 33

Ser Leu Ser Cys Arg Pro Pro Met Val Lys Leu Val Cys Pro Ala Xaa
1               5                   10                  15

Asn Xaa Arg Ala Glu Gly Leu Xaa Cys Xaa Lys Thr Cys Xaa Xaa Tyr
            20                  25                  30

Xaa Leu Xaa Cys Met Ser Xaa Gly Cys Val Ser Gly Cys Leu Cys Pro
        35                  40                  45

Pro Gly Met Val Arg His Xaa Xaa Arg Cys Val Ala Leu Xaa Arg Cys
50                  55                  60

Pro Cys Phe His Gln Gly Lys Xaa Tyr Ala Xaa Gly Glu Thr Val Lys
65                  70                  75                  80

Ile Gly Cys Asn Thr Cys Val Cys Arg Xaa Arg Lys Trp Asn Cys Thr
                85                  90                  95

Asp His Val Cys Asp Ala
            100

<210> SEQ ID NO 34
<211> LENGTH: 102
<212> TYPE: PRT
<213> ORGANISM: Artificial Sequence
<220> FEATURE:
<223> OTHER INFORMATION: modified D' domain
<220> FEATURE:
```

```
<221> NAME/KEY: MISC_FEATURE
<222> LOCATION: (16)..(16)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is any amino acid
<220> FEATURE:
<221> NAME/KEY: MISC_FEATURE
<222> LOCATION: (26)..(26)
<223> OTHER INFORMATION: Xaa is any amino acid
<220> FEATURE:
<221> NAME/KEY: MISC_FEATURE
<222> LOCATION: (30)..(30)
<223> OTHER INFORMATION: Xaa is any amino acid
<220> FEATURE:
<221> NAME/KEY: MISC_FEATURE
<222> LOCATION: (31)..(31)
<223> OTHER INFORMATION: Xaa is any amino acid
<220> FEATURE:
<221> NAME/KEY: MISC_FEATURE
<222> LOCATION: (39)..(39)
<223> OTHER INFORMATION: Xaa is any amino acid
<220> FEATURE:
<221> NAME/KEY: MISC_FEATURE
<222> LOCATION: (55)..(55)
<223> OTHER INFORMATION: Xaa is any amino acid
<220> FEATURE:
<221> NAME/KEY: MISC_FEATURE
<222> LOCATION: (56)..(56)
<223> OTHER INFORMATION: Xaa is any amino acid
<220> FEATURE:
<221> NAME/KEY: MISC_FEATURE
<222> LOCATION: (72)..(72)
<223> OTHER INFORMATION: Xaa is any amino acid
<220> FEATURE:
<221> NAME/KEY: MISC_FEATURE
<222> LOCATION: (75)..(75)
<223> OTHER INFORMATION: Xaa is any amino acid
<220> FEATURE:
<221> NAME/KEY: MISC_FEATURE
<222> LOCATION: (90)..(90)
<223> OTHER INFORMATION: Xaa is any amino acid

<400> SEQUENCE: 34

Ser Leu Ser Cys Arg Pro Pro Met Val Lys Leu Val Cys Pro Ala Xaa
1               5                   10                  15

Asn Xaa Arg Ala Glu Gly Leu Glu Cys Xaa Lys Thr Cys Xaa Xaa Tyr
            20                  25                  30

Asp Leu Glu Cys Met Ser Xaa Gly Cys Val Ser Gly Cys Leu Cys Pro
        35                  40                  45

Pro Gly Met Val Arg His Xaa Xaa Arg Cys Val Ala Leu Glu Arg Cys
    50                  55                  60

Pro Cys Phe His Gln Gly Lys Xaa Tyr Ala Xaa Gly Glu Thr Val Lys
65                  70                  75                  80

Ile Gly Cys Asn Thr Cys Val Cys Arg Xaa Arg Lys Trp Asn Cys Thr
                85                  90                  95

Asp His Val Cys Asp Ala
            100

<210> SEQ ID NO 35
<211> LENGTH: 102
<212> TYPE: PRT
<213> ORGANISM: Artificial Sequence
<220> FEATURE:
<223> OTHER INFORMATION: modified D' domain
<220> FEATURE:
<221> NAME/KEY: MISC_FEATURE
<222> LOCATION: (16)..(16)
<223> OTHER INFORMATION: Xaa is Asp or Asn
<220> FEATURE:
```

```
<221> NAME/KEY: MISC_FEATURE
<222> LOCATION: (18)..(18)
<223> OTHER INFORMATION: Xaa is Leu or Pro
<220> FEATURE:
<221> NAME/KEY: MISC_FEATURE
<222> LOCATION: (26)..(26)
<223> OTHER INFORMATION: Xaa is Thr or Ala
<220> FEATURE:
<221> NAME/KEY: MISC_FEATURE
<222> LOCATION: (30)..(30)
<223> OTHER INFORMATION: Xaa is Gln or Arg
<220> FEATURE:
<221> NAME/KEY: MISC_FEATURE
<222> LOCATION: (31)..(31)
<223> OTHER INFORMATION: Xaa is Asn or Lys
<220> FEATURE:
<221> NAME/KEY: MISC_FEATURE
<222> LOCATION: (39)..(39)
<223> OTHER INFORMATION: Xaa is Met or Arg or Lys
<220> FEATURE:
<221> NAME/KEY: MISC_FEATURE
<222> LOCATION: (55)..(55)
<223> OTHER INFORMATION: Xaa Glu or Ala or Lys
<220> FEATURE:
<221> NAME/KEY: MISC_FEATURE
<222> LOCATION: (56)..(56)
<223> OTHER INFORMATION: Xaa Asn or Lys
<220> FEATURE:
<221> NAME/KEY: MISC_FEATURE
<222> LOCATION: (72)..(72)
<223> OTHER INFORMATION: Xaa Glu or Gln
<220> FEATURE:
<221> NAME/KEY: MISC_FEATURE
<222> LOCATION: (75)..(75)
<223> OTHER INFORMATION: Xaa Pro or Lys
<220> FEATURE:
<221> NAME/KEY: MISC_FEATURE
<222> LOCATION: (90)..(90)
<223> OTHER INFORMATION: Xaa Asp or Asn

<400> SEQUENCE: 35

Ser Leu Ser Cys Arg Pro Pro Met Val Lys Leu Val Cys Pro Ala Xaa
1               5                   10                  15

Asn Xaa Arg Ala Glu Gly Leu Glu Cys Xaa Lys Thr Cys Xaa Xaa Tyr
            20                  25                  30

Asp Leu Glu Cys Met Ser Xaa Gly Cys Val Ser Gly Cys Leu Cys Pro
        35                  40                  45

Pro Gly Met Val Arg His Xaa Xaa Arg Cys Val Ala Leu Glu Arg Cys
    50                  55                  60

Pro Cys Phe His Gln Gly Lys Xaa Tyr Ala Xaa Gly Glu Thr Val Lys
65                  70                  75                  80

Ile Gly Cys Asn Thr Cys Val Cys Arg Xaa Arg Lys Trp Asn Cys Thr
                85                  90                  95

Asp His Val Cys Asp Ala
            100

<210> SEQ ID NO 36
<211> LENGTH: 2332
<212> TYPE: PRT
<213> ORGANISM: Homo sapiens

<400> SEQUENCE: 36

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45
```

```
Thr Leu Phe Val Glu Phe Thr Asp His Leu Phe Asn Ile Ala Lys Pro
 50                  55                  60

Arg Pro Pro Trp Met Gly Leu Leu Gly Pro Thr Ile Gln Ala Glu Val
 65                  70                  75                  80

Tyr Asp Thr Val Ile Thr Leu Lys Asn Met Ala Ser His Pro Val
                 85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
450                 455                 460
```

```
Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Arg Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
```

```
                885                 890                 895
Gly Thr Asp Asn Thr Ser Ser Leu Gly Pro Pro Ser Met Pro Val His
                    900                 905                 910
Tyr Asp Ser Gln Leu Asp Thr Thr Leu Phe Gly Lys Lys Ser Ser Pro
                    915                 920                 925
Leu Thr Glu Ser Gly Gly Pro Leu Ser Leu Ser Glu Asn Asn Asp
                930                 935                 940
Ser Lys Leu Leu Glu Ser Gly Leu Met Asn Ser Gln Glu Ser Ser Trp
945                 950                 955                 960
Gly Lys Asn Val Ser Ser Thr Glu Ser Gly Arg Leu Phe Lys Gly Lys
                965                 970                 975
Arg Ala His Gly Pro Ala Leu Leu Thr Lys Asp Asn Ala Leu Phe Lys
                980                 985                 990
Val Ser Ile Ser Leu Leu Lys Thr Asn Lys Thr Ser Asn Asn Ser Ala
                995                 1000                1005
Thr Asn Arg Lys Thr His Ile Asp Gly Pro Ser Leu Leu Ile Glu
    1010                1015                1020
Asn Ser Pro Ser Val Trp Gln Asn Ile Leu Glu Ser Asp Thr Glu
    1025                1030                1035
Phe Lys Lys Val Thr Pro Leu Ile His Asp Arg Met Leu Met Asp
    1040                1045                1050
Lys Asn Ala Thr Ala Leu Arg Leu Asn His Met Ser Asn Lys Thr
    1055                1060                1065
Thr Ser Ser Lys Asn Met Glu Met Val Gln Gln Lys Lys Glu Gly
    1070                1075                1080
Pro Ile Pro Pro Asp Ala Gln Asn Pro Asp Met Ser Phe Phe Lys
    1085                1090                1095
Met Leu Phe Leu Pro Glu Ser Ala Arg Trp Ile Gln Arg Thr His
    1100                1105                1110
Gly Lys Asn Ser Leu Asn Ser Gly Gln Gly Pro Ser Pro Lys Gln
    1115                1120                1125
Leu Val Ser Leu Gly Pro Glu Lys Ser Val Glu Gly Gln Asn Phe
    1130                1135                1140
Leu Ser Glu Lys Asn Lys Val Val Val Gly Lys Gly Glu Phe Thr
    1145                1150                1155
Lys Asp Val Gly Leu Lys Glu Met Val Phe Pro Ser Ser Arg Asn
    1160                1165                1170
Leu Phe Leu Thr Asn Leu Asp Asn Leu His Glu Asn Asn Thr His
    1175                1180                1185
Asn Gln Glu Lys Lys Ile Gln Glu Glu Ile Glu Lys Lys Glu Thr
    1190                1195                1200
Leu Ile Gln Glu Asn Val Val Leu Pro Gln Ile His Thr Val Thr
    1205                1210                1215
Gly Thr Lys Asn Phe Met Lys Asn Leu Phe Leu Leu Ser Thr Arg
    1220                1225                1230
Gln Asn Val Glu Gly Ser Tyr Asp Gly Ala Tyr Ala Pro Val Leu
    1235                1240                1245
Gln Asp Phe Arg Ser Leu Asn Asp Ser Thr Asn Arg Thr Lys Lys
    1250                1255                1260
His Thr Ala His Phe Ser Lys Lys Gly Glu Glu Asn Leu Glu
    1265                1270                1275
Gly Leu Gly Asn Gln Thr Lys Gln Ile Val Glu Lys Tyr Ala Cys
    1280                1285                1290
```

```
Thr Thr Arg Ile Ser Pro Asn Thr Ser Gln Gln Asn Phe Val Thr
    1295            1300            1305

Gln Arg Ser Lys Arg Ala Leu Lys Gln Phe Arg Leu Pro Leu Glu
    1310            1315            1320

Glu Thr Glu Leu Glu Lys Arg Ile Ile Val Asp Asp Thr Ser Thr
    1325            1330            1335

Gln Trp Ser Lys Asn Met Lys His Leu Thr Pro Ser Thr Leu Thr
    1340            1345            1350

Gln Ile Asp Tyr Asn Glu Lys Glu Lys Gly Ala Ile Thr Gln Ser
    1355            1360            1365

Pro Leu Ser Asp Cys Leu Thr Arg Ser His Ser Ile Pro Gln Ala
    1370            1375            1380

Asn Arg Ser Pro Leu Pro Ile Ala Lys Val Ser Ser Phe Pro Ser
    1385            1390            1395

Ile Arg Pro Ile Tyr Leu Thr Arg Val Leu Phe Gln Asp Asn Ser
    1400            1405            1410

Ser His Leu Pro Ala Ala Ser Tyr Arg Lys Lys Asp Ser Gly Val
    1415            1420            1425

Gln Glu Ser Ser His Phe Leu Gln Gly Ala Lys Lys Asn Asn Leu
    1430            1435            1440

Ser Leu Ala Ile Leu Thr Leu Glu Met Thr Gly Asp Gln Arg Glu
    1445            1450            1455

Val Gly Ser Leu Gly Thr Ser Ala Thr Asn Ser Val Thr Tyr Lys
    1460            1465            1470

Lys Val Glu Asn Thr Val Leu Pro Lys Pro Asp Leu Pro Lys Thr
    1475            1480            1485

Ser Gly Lys Val Glu Leu Leu Pro Lys Val His Ile Tyr Gln Lys
    1490            1495            1500

Asp Leu Phe Pro Thr Glu Thr Ser Asn Gly Ser Pro Gly His Leu
    1505            1510            1515

Asp Leu Val Glu Gly Ser Leu Leu Gln Gly Thr Glu Gly Ala Ile
    1520            1525            1530

Lys Trp Asn Glu Ala Asn Arg Pro Gly Lys Val Pro Phe Leu Arg
    1535            1540            1545

Val Ala Thr Glu Ser Ser Ala Lys Thr Pro Ser Lys Leu Leu Asp
    1550            1555            1560

Pro Leu Ala Trp Asp Asn His Tyr Gly Thr Gln Ile Pro Lys Glu
    1565            1570            1575

Glu Trp Lys Ser Gln Glu Lys Ser Pro Glu Lys Thr Ala Phe Lys
    1580            1585            1590

Lys Lys Asp Thr Ile Leu Ser Leu Asn Ala Cys Glu Ser Asn His
    1595            1600            1605

Ala Ile Ala Ala Ile Asn Glu Gly Gln Asn Lys Pro Glu Ile Glu
    1610            1615            1620

Val Thr Trp Ala Lys Gln Gly Arg Thr Glu Arg Leu Cys Ser Gln
    1625            1630            1635

Asn Pro Pro Val Leu Lys Arg His Gln Arg Glu Ile Thr Arg Thr
    1640            1645            1650

Thr Leu Gln Ser Asp Gln Glu Glu Ile Asp Tyr Asp Asp Thr Ile
    1655            1660            1665

Ser Val Glu Met Lys Lys Glu Asp Phe Asp Ile Tyr Asp Glu Asp
    1670            1675            1680
```

-continued

| | | | | | | | | | | | |
|---|---|---|---|---|---|---|---|---|---|---|---|
| Glu | Asn | Gln | Ser | Pro | Arg | Ser | Phe | Gln | Lys | Lys | Thr | Arg | His | Tyr |
| 1685 | | | | 1690 | | | | | 1695 | | |

Glu Asn Gln Ser Pro Arg Ser Phe Gln Lys Lys Thr Arg His Tyr
1685              1690               1695

Phe Ile Ala Ala Val Glu Arg Leu Trp Asp Tyr Gly Met Ser Ser
1700              1705               1710

Ser Pro His Val Leu Arg Asn Arg Ala Gln Ser Gly Ser Val Pro
1715              1720               1725

Gln Phe Lys Lys Val Val Phe Gln Glu Phe Thr Asp Gly Ser Phe
1730              1735               1740

Thr Gln Pro Leu Tyr Arg Gly Glu Leu Asn Glu His Leu Gly Leu
1745              1750               1755

Leu Gly Pro Tyr Ile Arg Ala Glu Val Glu Asp Asn Ile Met Val
1760              1765               1770

Thr Phe Arg Asn Gln Ala Ser Arg Pro Tyr Ser Phe Tyr Ser Ser
1775              1780               1785

Leu Ile Ser Tyr Glu Glu Asp Gln Arg Gln Gly Ala Glu Pro Arg
1790              1795               1800

Lys Asn Phe Val Lys Pro Asn Glu Thr Lys Thr Tyr Phe Trp Lys
1805              1810               1815

Val Gln His His Met Ala Pro Thr Lys Asp Glu Phe Asp Cys Lys
1820              1825               1830

Ala Trp Ala Tyr Phe Ser Asp Val Asp Leu Glu Lys Asp Val His
1835              1840               1845

Ser Gly Leu Ile Gly Pro Leu Leu Val Cys His Thr Asn Thr Leu
1850              1855               1860

Asn Pro Ala His Gly Arg Gln Val Thr Val Gln Glu Phe Ala Leu
1865              1870               1875

Phe Phe Thr Ile Phe Asp Glu Thr Lys Ser Trp Tyr Phe Thr Glu
1880              1885               1890

Asn Met Glu Arg Asn Cys Arg Ala Pro Cys Asn Ile Gln Met Glu
1895              1900               1905

Asp Pro Thr Phe Lys Glu Asn Tyr Arg Phe His Ala Ile Asn Gly
1910              1915               1920

Tyr Ile Met Asp Thr Leu Pro Gly Leu Val Met Ala Gln Asp Gln
1925              1930               1935

Arg Ile Arg Trp Tyr Leu Leu Ser Met Gly Ser Asn Glu Asn Ile
1940              1945               1950

His Ser Ile His Phe Ser Gly His Val Phe Thr Val Arg Lys Lys
1955              1960               1965

Glu Glu Tyr Lys Met Ala Leu Tyr Asn Leu Tyr Pro Gly Val Phe
1970              1975               1980

Glu Thr Val Glu Met Leu Pro Ser Lys Ala Gly Ile Trp Arg Val
1985              1990               1995

Glu Cys Leu Ile Gly Glu His Leu His Ala Gly Met Ser Thr Leu
2000              2005               2010

Phe Leu Val Tyr Ser Asn Lys Cys Gln Thr Pro Leu Gly Met Ala
2015              2020               2025

Ser Gly His Ile Arg Asp Phe Gln Ile Thr Ala Ser Gly Gln Tyr
2030              2035               2040

Gly Gln Trp Ala Pro Lys Leu Ala Arg Leu His Tyr Ser Gly Ser
2045              2050               2055

Ile Asn Ala Trp Ser Thr Lys Glu Pro Phe Ser Trp Ile Lys Val
2060              2065               2070

Asp Leu Leu Ala Pro Met Ile Ile His Gly Ile Lys Thr Gln Gly

-continued

```
              2075                2080                2085
Ala Arg Gln Lys Phe Ser Ser Leu Tyr Ile Ser Gln Phe Ile Ile
        2090                2095                2100
Met Tyr Ser Leu Asp Gly Lys Lys Trp Gln Thr Tyr Arg Gly Asn
        2105                2110                2115
Ser Thr Gly Thr Leu Met Val Phe Phe Gly Asn Val Asp Ser Ser
        2120                2125                2130
Gly Ile Lys His Asn Ile Phe Asn Pro Pro Ile Ile Ala Arg Tyr
        2135                2140                2145
Ile Arg Leu His Pro Thr His Tyr Ser Ile Arg Ser Thr Leu Arg
        2150                2155                2160
Met Glu Leu Met Gly Cys Asp Leu Asn Ser Cys Ser Met Pro Leu
        2165                2170                2175
Gly Met Glu Ser Lys Ala Ile Ser Asp Ala Gln Ile Thr Ala Ser
        2180                2185                2190
Ser Tyr Phe Thr Asn Met Phe Ala Thr Trp Ser Pro Ser Lys Ala
        2195                2200                2205
Arg Leu His Leu Gln Gly Arg Ser Asn Ala Trp Arg Pro Gln Val
        2210                2215                2220
Asn Asn Pro Lys Glu Trp Leu Gln Val Asp Phe Gln Lys Thr Met
        2225                2230                2235
Lys Val Thr Gly Val Thr Thr Gln Gly Val Lys Ser Leu Leu Thr
        2240                2245                2250
Ser Met Tyr Val Lys Glu Phe Leu Ile Ser Ser Ser Gln Asp Gly
        2255                2260                2265
His Gln Trp Thr Leu Phe Phe Gln Asn Gly Lys Val Lys Val Phe
        2270                2275                2280
Gln Gly Asn Gln Asp Ser Phe Thr Pro Val Val Asn Ser Leu Asp
        2285                2290                2295
Pro Pro Leu Leu Thr Arg Tyr Leu Arg Ile His Pro Gln Ser Trp
        2300                2305                2310
Val His Gln Ile Ala Leu Arg Met Glu Val Leu Gly Cys Glu Ala
        2315                2320                2325
Gln Asp Leu Tyr
        2330

<210> SEQ ID NO 37
<211> LENGTH: 1444
<212> TYPE: PRT
<213> ORGANISM: artificial sequence
<220> FEATURE:
<223> OTHER INFORMATION: mature single chain Factor VIII

<400> SEQUENCE: 37

Ala Thr Arg Arg Tyr Tyr Leu Gly Ala Val Glu Leu Ser Trp Asp Tyr
1               5                   10                  15
Met Gln Ser Asp Leu Gly Glu Leu Pro Val Asp Ala Arg Phe Pro Pro
            20                  25                  30
Arg Val Pro Lys Ser Phe Pro Phe Asn Thr Ser Val Val Tyr Lys Lys
        35                  40                  45
Thr Leu Phe Val Glu Phe Thr Asp His Leu Phe Asn Ile Ala Lys Pro
    50                  55                  60
Arg Pro Pro Trp Met Gly Leu Leu Gly Pro Thr Ile Gln Ala Glu Val
65                  70                  75                  80
Tyr Asp Thr Val Val Ile Thr Leu Lys Asn Met Ala Ser His Pro Val
```

```
                     85                  90                  95
Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
                115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
                180                 185                 190

His Lys Phe Ile Leu Leu Phe Ala Val Phe Asp Glu Gly Lys Ser Trp
                195                 200                 205

His Ser Glu Thr Lys Asn Ser Leu Met Gln Asp Arg Asp Ala Ala Ser
                210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
                275                 280                 285

Ser Pro Ile Thr Phe Leu Thr Ala Gln Thr Leu Leu Met Asp Leu Gly
                290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asp Asn Ser Pro Ser Phe
                355                 360                 365

Ile Gln Ile Arg Ser Val Ala Lys Lys His Pro Lys Thr Trp Val His
                370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
                435                 440                 445

Leu Gly Pro Leu Leu Tyr Gly Glu Val Gly Asp Thr Leu Leu Ile Ile
                450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510
```

```
Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
                595                 600                 605

Gln Ala Ser Asn Ile Met His Ser Ile Asn Gly Tyr Val Phe Asp Ser
                610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
                675                 680                 685

Ile Leu Gly Cys His Asn Ser Asp Phe Arg Asn Arg Gly Met Thr Ala
                690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Arg Ser Thr Arg
                740                 745                 750

Gln Lys Gln Phe Asn Ala Thr Thr Ile Pro Glu Asn Thr Thr Leu Gln
                755                 760                 765

Ser Asp Gln Glu Glu Ile Asp Tyr Asp Asp Thr Ile Ser Val Glu Met
770                 775                 780

Lys Lys Glu Asp Phe Asp Ile Tyr Asp Glu Asp Glu Asn Gln Ser Pro
785                 790                 795                 800

Arg Ser Phe Gln Lys Lys Thr Arg His Tyr Phe Ile Ala Ala Val Glu
                805                 810                 815

Arg Leu Trp Asp Tyr Gly Met Ser Ser Ser Pro His Val Leu Arg Asn
                820                 825                 830

Arg Ala Gln Ser Gly Ser Val Pro Gln Phe Lys Lys Val Val Phe Gln
                835                 840                 845

Glu Phe Thr Asp Gly Ser Phe Thr Gln Pro Leu Tyr Arg Gly Glu Leu
850                 855                 860

Asn Glu His Leu Gly Leu Leu Gly Pro Tyr Ile Arg Ala Glu Val Glu
865                 870                 875                 880

Asp Asn Ile Met Val Thr Phe Arg Asn Gln Ala Ser Arg Pro Tyr Ser
                885                 890                 895

Phe Tyr Ser Ser Leu Ile Ser Tyr Glu Glu Asp Gln Arg Gln Gly Ala
                900                 905                 910

Glu Pro Arg Lys Asn Phe Val Lys Pro Asn Glu Thr Lys Thr Tyr Phe
                915                 920                 925
```

-continued

Trp Lys Val Gln His His Met Ala Pro Thr Lys Asp Glu Phe Asp Cys
930                 935                 940

Lys Ala Trp Ala Tyr Phe Ser Asp Val Asp Leu Glu Lys Asp Val His
945                 950                 955                 960

Ser Gly Leu Ile Gly Pro Leu Val Cys His Thr Asn Thr Leu Asn
            965                 970                 975

Pro Ala His Gly Arg Gln Val Thr Val Gln Glu Phe Ala Leu Phe Phe
                980                 985                 990

Thr Ile Phe Asp Glu Thr Lys Ser Trp Tyr Phe Thr Glu Asn Met Glu
            995                 1000                1005

Arg Asn Cys Arg Ala Pro Cys Asn Ile Gln Met Glu Asp Pro Thr
1010                1015                1020

Phe Lys Glu Asn Tyr Arg Phe His Ala Ile Asn Gly Tyr Ile Met
1025                1030                1035

Asp Thr Leu Pro Gly Leu Val Met Ala Gln Asp Gln Arg Ile Arg
1040                1045                1050

Trp Tyr Leu Leu Ser Met Gly Ser Asn Glu Asn Ile His Ser Ile
1055                1060                1065

His Phe Ser Gly His Val Phe Thr Val Arg Lys Lys Glu Glu Tyr
1070                1075                1080

Lys Met Ala Leu Tyr Asn Leu Tyr Pro Gly Val Phe Glu Thr Val
1085                1090                1095

Glu Met Leu Pro Ser Lys Ala Gly Ile Trp Arg Val Glu Cys Leu
1100                1105                1110

Ile Gly Glu His Leu His Ala Gly Met Ser Thr Leu Phe Leu Val
1115                1120                1125

Tyr Ser Asn Lys Cys Gln Thr Pro Leu Gly Met Ala Ser Gly His
1130                1135                1140

Ile Arg Asp Phe Gln Ile Thr Ala Ser Gly Gln Tyr Gly Gln Trp
1145                1150                1155

Ala Pro Lys Leu Ala Arg Leu His Tyr Ser Gly Ser Ile Asn Ala
1160                1165                1170

Trp Ser Thr Lys Glu Pro Phe Ser Trp Ile Lys Val Asp Leu Leu
1175                1180                1185

Ala Pro Met Ile Ile His Gly Ile Lys Thr Gln Gly Ala Arg Gln
1190                1195                1200

Lys Phe Ser Ser Leu Tyr Ile Ser Gln Phe Ile Ile Met Tyr Ser
1205                1210                1215

Leu Asp Gly Lys Lys Trp Gln Thr Tyr Arg Gly Asn Ser Thr Gly
1220                1225                1230

Thr Leu Met Val Phe Phe Gly Asn Val Asp Ser Ser Gly Ile Lys
1235                1240                1245

His Asn Ile Phe Asn Pro Pro Ile Ile Ala Arg Tyr Ile Arg Leu
1250                1255                1260

His Pro Thr His Tyr Ser Ile Arg Ser Thr Leu Arg Met Glu Leu
1265                1270                1275

Met Gly Cys Asp Leu Asn Ser Cys Ser Met Pro Leu Gly Met Glu
1280                1285                1290

Ser Lys Ala Ile Ser Asp Ala Gln Ile Thr Ala Ser Ser Tyr Phe
1295                1300                1305

Thr Asn Met Phe Ala Thr Trp Ser Pro Ser Lys Ala Arg Leu His
1310                1315                1320

Leu Gln Gly Arg Ser Asn Ala Trp Arg Pro Gln Val Asn Asn Pro

```
            1325                1330                1335

Lys Glu Trp Leu Gln Val Asp Phe Gln Lys Thr Met Lys Val Thr
        1340                1345                1350

Gly Val Thr Thr Gln Gly Val Lys Ser Leu Leu Thr Ser Met Tyr
    1355                1360                1365

Val Lys Glu Phe Leu Ile Ser Ser Ser Gln Asp Gly His Gln Trp
1370                1375                1380

Thr Leu Phe Phe Gln Asn Gly Lys Val Lys Val Phe Gln Gly Asn
    1385                1390                1395

Gln Asp Ser Phe Thr Pro Val Val Asn Ser Leu Asp Pro Pro Leu
1400                1405                1410

Leu Thr Arg Tyr Leu Arg Ile His Pro Gln Ser Trp Val His Gln
    1415                1420                1425

Ile Ala Leu Arg Met Glu Val Leu Gly Cys Glu Ala Gln Asp Leu
    1430                1435                1440

Tyr

<210> SEQ ID NO 38
<211> LENGTH: 585
<212> TYPE: PRT
<213> ORGANISM: Homo sapiens

<400> SEQUENCE: 38

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
```

```
            245                 250                 255
Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
                355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
                435                 440                 445

Ala Glu Asp Tyr Leu Ser Val Val Leu Asn Gln Leu Cys Val Leu His
                450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
                530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585
```